US008457745B1

(12) United States Patent
Garcia et al.

(10) Patent No.: US 8,457,745 B1
(45) Date of Patent: Jun. 4, 2013

(54) METHOD, SYSTEM AND APPARATUS FOR CONTROL OF PANCREATIC BETA CELL FUNCTION TO IMPROVE GLUCOSE HOMEOSTATIS AND INSULIN PRODUCTION

(71) Applicants: Julio Luis Garcia, Coral Gables, FL (US); Oresteban Carabeo, Miami Gardens, FL (US); Ruben Valdes, Beverly Hills, FL (US); Robert Valdes, Miami Lakes, FL (US)

(72) Inventors: Julio Luis Garcia, Coral Gables, FL (US); Oresteban Carabeo, Miami Gardens, FL (US); Ruben Valdes, Beverly Hills, FL (US); Robert Valdes, Miami Lakes, FL (US)

( * ) Notice: Subject to any disclaimer, the term of this patent is extended or adjusted under 35 U.S.C. 154(b) by 0 days.

(21) Appl. No.: 13/663,658

(22) Filed: Oct. 30, 2012

Related U.S. Application Data

(60) Provisional application No. 61/619,352, filed on Apr. 2, 2012.

(51) Int. Cl.
*A61N 1/36* (2006.01)
(52) U.S. Cl.
USPC .......................................................... 607/40

(58) Field of Classification Search
None
See application file for complete search history.

(56) References Cited

U.S. PATENT DOCUMENTS

| | | | |
|---|---|---|---|
| 7,477,944 | B1 | 1/2009 | Whitehurst et al. |
| 2002/0026141 | A1 | 2/2002 | Houben et al. |
| 2011/0230939 | A1 | 9/2011 | Weinstock |

FOREIGN PATENT DOCUMENTS

WO WO 2012/083259 A2 6/2012

*Primary Examiner* — Carl H Layno
*Assistant Examiner* — Paula J Stice
(74) *Attorney, Agent, or Firm* — Melvin K. Silverman

(57) ABSTRACT

A therapeutic waveform for neurophysiologic treatment of conditions associated with function of ionic channels of beta cells of the pancreas includes a positive part having a pulse width of 40 to 60 milliseconds having a positively pointing segment, and includes a negative part dropping sharply negatively following the positive part. The negative drop is 75 to 90 percent of the peak-to-peak voltage of the waveform at about 10 to 100 volts AC. A negative spike-like first aspect of the negative part exhibits a pulse width of 40 to 60 milliseconds but afterwards gradually approaches a neutral voltage level of the waveform. The first aspect of the negative part of the waveform is followed by a second aspect which more slowly approaches the neutral level over a period of 100 to 200 milliseconds, before the next waveform. The current of the waveform is 300 to 1000 micro-amperes.

22 Claims, 24 Drawing Sheets

PEAK CALCIUM CURRENT

INTERNAL FREE $Ca^{2+}$ (d) Convergence, single source (e) Reverberating circuit (f) Parallel after-discharge circuit

METHOD, SYSTEM AND APPARATUS FOR CONTROL OF PANCREATIC BETA CELL FUNCTION TO IMPROVE GLUCOSE HOMEOSTATIS AND INSULIN PRODUCTION

CROSS REFERENCE TO RELATED APPLICATION

This application claims the benefit under 35 USC 119(e) of the provisional patent application Ser. No. 61/619,352 filed Apr. 2, 2012, and the same is incorporated herewith in its entirety.

BACKGROUND OF THE INVENTION

As is well-known, the sympathetic nervous system (SNS) is a branch of the autonomic nervous system (ANS) and of the central nervous system (CNS) and is related to the parasympathetic nervous system (PNS).

The SNS is active at a so-called basal level and becomes active during times of stress. As such, this stress response is termed the fight-or-flight response. The SNS operates through a series of interconnected neurons. Sympathetic neurons are frequently considered part of the PNS, although many lie within the CNS. Sympathetic neurons of the spinal cord are, of course, part of the CNS, and communicate with peripheral sympathetic neurons through a series of sympathetic ganglia. For purposes of the present invention, the CNS may be viewed (see FIG. 1) as consisting of a spinal cord 10 and a sympathetic trunk 12 thereof.

The PNS is shown to the right of FIG. 1 as numeral 14. The PNS is considered an automatic regulation system, that is, one that operates without the intervention of conscious thought. As such, fibers of the PNS innervate tissues in almost every organ system, providing at least some regulatory function to areas as diverse as the diameter of the eye, gut motility, and urinary output. For purposes of the present invention, the only organs so regulated by the SNS shown are lung 16, hair follicles 18, liver 20, gall bladder 22, pancreas 24, adrenal glands 26, and management of hypertension generally. As may be noted in FIG. 1, all neurons of nerves of the thoracic vertebrae of the spinal cord pass through sympathetic trunk 12 thereof. This is known as the thoracolumbar outflow of the SNS. Therein, axons of these nerves leave the spinal cord through anterior outlets/routes thereof of the sympathetic trunk 12 and, certain groups thereof, including the groups emanating from thoracic vertebrae, reach celiac ganglion 28 before dispersing to various internal organs in the thoracic region of the body including the pancreas 24. From these internal organs occurs a flow of axons of these respective nerves to the base of the PNS at the vagus nerve 30 shown in FIG. 1, further discussed below.

To reach target organs and glands, axons must travel long distances in the body, and to accomplish this, many axons relay their message through a second process known as synaptic transmission. This entails the use of neuro-transmitters across what is termed the synaptic cleft which activates further cells known as post-synaptic cells. Therefrom, the message is carried to the final destination in the target organ, in this case the pancreas.

It is known that messages travel through the SNS in a bi-directional fashion. That is, so-called efferent messages can trigger changes in different parts of the body simultaneously to further the above referenced fight-or-flight response function of the SNS. It is noted that the PNS, in distinction to the CNS, controls actions that can be summarized as rest-and-digest, as opposed to the fight-or-flight effects of the SNS. Therefore, many functions of the internal organs are controlled by the PNS in that such actions do not require immediate reaction, as do those of the SNS. Included within these is the control of the gall bladder 22 and pancreas 24 as may be noted in FIG. 1.

It may thereby be appreciated that the autonomic nervous system includes both said SNS and PNS divisions which, collectively, regulate the body's visceral organs, their nerves and tissues of various types. The SNS and PNS must, of necessity, operate in tandem to create synergistic effects that are not merely an "on" or "off" function but which can better be described as a continuum of effect depending upon how vigorously each division must execute its function in response to given conditions. The PNS often operates through what are known as parasympathetic ganglia and includes so-called terminal ganglia and intramural ganglia which lie near the organs which they innervate, this inclusive of the pancreas.

The subject of FIG. 1 is shown in greater detail in FIG. 2 which shows extensions of the vagus nerve 30, known as the anterior and posterior vagus trunks 32 and right sympathetic trunk 33. Vagus nerve 30 and its offshoots are shown in yet further detail in FIG. 3 which also shows the pathways of the efferent fibers, afferent fibers and parasympathetic fibers of the CNS. More particularly, FIG. 3 shows the meningeal branch 34 of vagus nerve 30, the auricular branch 36, posterior nucleus 38 of the vagus nerve, superior ganglion 40 thereof, interior ganglion 42 thereof, pharyngeal branch 44, communicating branch 46 of the vagus nerve, superior cervical cardiac branch 48, inferior cardiac branch 50 and thoracic cardiac branch 52 of the vagus nerve. There may be appreciated the extensive role of the vagus nerve, its offshoots in human physiology and the many neural pathways—efferent, afferent, and parasympathetic, enabled by the functions of the vagus nerve.

As is shown in FIG. 2, many elements of the vagus extend downwardly, through vagus trunks 32, and into the other major parts of the celiac ganglion 28.

In FIG. 4 is shown the range of vagus nerve innervation which includes the pancreas.

The pancreas proper is shown in FIG. 5 together with the celiac axis 54 which extends from celiac ganglion 28. (See FIG. 2). Therefrom it may be seen that the pancreas is a large organ situated below the diaphragm, above the kidneys, to the right of the intestine, and with the circulatory system through the pancreatic duct 56.

The CNS is activated mainly by nerve centers located in the spinal cord, brainstem, and hypothalamus. Autonomic nerves are formed by nerves of efferent fibers (See FIG. 3) leaving the CNS (less the striated muscles); there are some efferent fibers that transmit information of the ANS.

Signals that fall in the autonomic ganglia spinal cord, brain stem, and the hypothalamus 78, produce appropriate reflex responses that are returned to the bodies to monitor their activities.

Functionality the (SNS) is divided into the sympathetic in which adrenaline and noradrenaline are used as neurotransmitters; formed by the SNS trunk 12 and other prevertebral ganglia attached to the front side of the aorta. These include the celiac ganglia 28, renal aortic mesenteric upper and lower. See FIGS. 1-3.

The PNS is formed by isolated ganglia that use acetylcholine as a neurotransmitter, is responsible for storing and conserving energy, and maintains the body in normal situations. It always appears as an antagonist of the SNS, controlling involuntary acts. Its nerves are carried in the cranial nerves including the vagus 30 and its offshoots, as discussed above.

The spinal cord includes the sacral roots of S2 whose neurotransmitter is acetylcholine.

Sympathetic nerves originate in the spinal cord segments T1 to T2 (see FIG. 1) of the sympathetic chain (SNS) and proceed to the tissues and organs from the neuron pregangli-onic. Its axons pass through the root of the spinal cord corresponding to the spinal nerves. Therefrom preganglionick sympathetic fibers pass though the branch to one of the ganglia of the SNS, such that they then take one of the two following paths:

A. To neurons synapses, postganglionic of the ganglion which it penetrates. And

B. Up and down the SNS chain to generate synapses in other ganglia at varying distances and then through one of the sympathetic nerves coming out of the chain ending in one of the pre-aortic branches 48/50 (see FIG. 3) that innervates it. The SNS originates at different segments of the spinal cord, not necessarily directed to the same parts of the body as with the somatic spinal nerve fibers coming from the same vertebrae. Thus one sees that in the spinal segment T5 is associated with the SNS chain from the head T2 to the neck including T3 to T6. See FIG. 1. T7 to T11 go to the abdomen and then T12 to L2 go to the pelvis and legs.

The distribution of the sympathetic nerves to each organ is determined by the position that of the organ in the embryo when it originates.

The PNS and its fibers enter the CNS through sympathetic trunk 33 and the Cranial Nerves III, VII, IX, and X although like the SNS, it does not have pre- and post-ganglionic neurons. See FIG. 2.

The preganglia fibers travel through, without interruption, all the way to the tissue that it innervates. In the wall of the nerves are the neurons (postganglionic). Postganglionic fibers make synapses and spread throughout the body (some 1 millimeters to a few centimeters).

The parasympathetic innervation of the intestine runs through the vagus nerve and sacral nerves in the pelvis producing among other stimulation of the exocrine secretions of glandular epithelium, with an increase in the secretion of gastrin, secretion, and insulin. See FIG. 4.

It is noted that insulin is released only by beta cells in pancreatic Islets (i.e., small isolated masses of one type of tissue within a different type), known as the Islets of Langerhans. Insulin is one of the endocrine system secretions (i.e., secretions that are distributed in the body by way of the bloodstream) of the Islets of Langerhans, which helps integrate and control bodily metabolic activity. The Islets also include alpha cells, which produce glucagon, delta cells which produce somatostatin, and a small number of PP cells which produce pancreatic polypeptide ("PP"). The beta cells tend to be in the center of the pancreatic Islets, while the alpha cells tend to occupy the periphery. The beta cells generally constitute 60-70% of the Islets, the alpha cells 20-25%, and the delta cells approximately 10% Gap junctions exist between neighboring islet cells, permitting the ready flow of molecules and electrical current between cells. If these gap junctions are disrupted, insulin secretion is markedly reduced. Islet cell clusters function better as electrical than biochemical syncytia.

Under normal circumstances, insulin is secreted by the beta cells in response to an elevated level of plasma glucose via the following steps. The transportation of glucose across the beta cell membrane is facilitated by a specific transporter molecule known as GLUT-2. Once inside the beta cell, the enzyme glucokinase causes glucose to phosphorylate (i.e., to take up or combine with phosphoric acid or a phosphorus-containing group), which prevents its efflux. High levels of glucose and glucose-6-phosphate within the cell lead to a rapid increase in the ratio of adenosine triphosphate (ATP) to adenosine diphosphate (ADP), which leads directly to the closure of ATP-sensitive transmembrane potassium ion (K+) channels. This prevents the normal efflux of K+ from the beta cell, and the cell depolarizes, i.e., closing of some ionic channels. Voltage-regulated calcium ion (Ca++) channels open in response to this depolarization, allowing an influx of Ca++. Elevated intracellular Ca++ leads to activation of protein kinases and ultimately to fusion of insulin-containing secretory granules with the beta cell membrane, thus leading to exocytosis of insulin into the systemic circulation. This entire sequence occurs within one minute of exposure to elevated glucose levels.

Insulin is a hormone that serves a variety of functions, the primary action of which is to potentiate the uptake of glucose from the bloodstream by muscle and adipose tissue. It also promotes conversion of glucose to a storage form (i.e., glucagon) in the liver and to fat in adipose tissue. These actions serve to decrease the circulating level of glucose.

Glucagon is released primarily under conditions of hypoglycemia, and it tends to have effects opposite those of insulin. Release of glucagon is also promoted by alpha-adrenergic neurotransmitters, and it is inhibited by beta-adrenergic neurotransmitters, cholinergic neutransmitters, and insulin.

Somatostatin secretion is stimulated by glucose, glucagon, beta-adrenergic neurotransmitters, cholinergic neurotransmitters, and a number of other chemical factors; its release is inhibited by insulin and by alpha-adrenergic neurotransmitters. Somatostain tends to inhibit the release of both insulin and glucagon.

Parasympathetic Stimulation

Secretion of insulin may also be modulated by other neural and chemical factors. Parasympathetic stimulation and the consequent release of acetylcholine tends to increase the secretion of insulin. Sympathetic stimulation produces competing effects, as beta-adrenergic neurotransmitters tend to increase insulin secretion while alpha-adrenergic neurotransmitters tend to decrease insulin secretion. Insulin secretion is also increased by a number of other factors, including K+, Ca++, arginine, lysine, glucagon-like peptide 1, gastric inhibitory peptide (GIP), secretion, cholecystokinin (CCK), and beta-3-agonists. Insulin secretion is also decreased by a number of other factors, including somatostatin, galanin, pancrestatin, and leptin.

As above noted, a significant body of research exists describing the influence of parasympathetic activity on insulin secretion by the pancreatic beta cells. Parasympathetic nerve stimulation in the dog produces a marked increase in insulin secretion and a moderate increase in glucagon secretion. In addition, parasympathetic activation produces increased insulin and glucagon secretion in proportion to pulse frequency, while inhibiting somatostatin release. Cholinergic neurotransmitters, which are the neurotransmitters most commonly secreted by parasympathetic nerve fibers, were found to be responsible for this influence. However, findings also suggest that a non-cholinergic neurotransmitter(s) may also be involved in parasympathetic regulation of pancreatic hormone secretion.

The specific parasympathetic pathways innervating the pancreatic Islets are known. Three branches of the vagus nerve mediate both insulin and glucagon release. The posterior gastric branch (198% and 117% increase from basal for insulin and glucagon, respectively), the anterior gastric branch (177% insulin increase and 104% glucagon increase), and the hepatic branch (103% insulin increase the 60% glucagon increase). In contrast, unreliable and insignificant hormonal responses were produced by electrical stimulation of fibers projecting from two other branches of the vagus nerve: the posterior celiac branch (12% insulin increase and 12% glucagon increase) and the accessory celiac branch (15% insulin increase and 31% glucagon increase).

Sympathetic Stimulation

The sympathetic nervous system also exerts a significant influence on insulin and glucagon secretion by the pancreatic Islets. The sympathetic splanchnic nerve, arising from the paraspinal sympathetic trunks, is the primary sympathetic influence on the pancreas. Its primary neurotransmitter is norepinephrine, which activates alpha-adrenergic and beta-1-adrenergic receptors, but has relatively little influence on beta-2-adrenergic receptors.

The pancreas is comprised mostly of acini and the Islets of Langerhans. Acini comprises over 80% of the gland. Each acinus is lined with wedge-shaped acinar cells. Acinar cells are the site of production and secretion of the digestive enzymes.

Capillaries allow hormones from the Islet cells to reach the acinar cells. Islets of Langerhans are scattered irregularly throughout the pancreas and contain the Islet cells, which are responsible for secreting the endocrine hormones: insulins, glucagon, somatostatin, and pancreatic, polypeptides. The insulin-secreting beta cells comprise about 60-70% of the Islet. They are surrounded by a mantle of glucagon-secreting alpha cells, somatostatin-secreting delta cells, and pancreatic polypeptide-secreting PP cells. The various cells of the Islets are separated from another by a rich capillary network.

The present invention provides electrical stimulation to at least one or more of the above mentioned areas as a treatment for diabetes. It is known that cells of the human body are acutely responsive to electrical and electromagnetic stimulation through neurotransmitters and otherwise, as has long been established by research in the area. Calcium has been determined to be the final transmitter of electrical signals to the cytoplasm of human cells. More particularly, changes in cell membrane potential are sensed by numerous calcium-sensing proteins of cell membrane which determine whether to open or close responsive to a charge carrying elements, in this case, the calcium anion $Ca^{2+}$. This is shown conceptually in FIG. 6 which shows the electrical call-to-action of a cell upon its sensing of a voltage gradient carried or created by a calcium anion. Stated otherwise, calcium anions transduce electrical signals to the cells through what are termed voltage-gated calcium channels (see Hille, "Ion Channels of Excitable Membranes," 3 Ed., 2001, Chap. 4). It is now recognized that electrical signaling of voltage-gated channels (of which there are many categories) of human cell membranes is controlled by intracellular free calcium (and other) ionic concentrations, and that electrical signals are modulated by the flow of calcium and other anions into cytoplasm from the external medium or from intra cellular stores through ionic specific channels.

These channels act as gates, in which concept of an "ion channel" was first proposed in the year 1950, that these channels represent a wide variety of biological processes, and rapid changes in the cells:

Contraction of the muscle, transport of nutrients, activation of (T) lymphocytes, the release of insulin by the beta cells of the pancreas, and cellular osteogenesis occur.

Differentiation, remodeling or hypertrophy, among other functions also occur. Ionic channels have two important characteristics:

1. Conduction of ions.
2. Recognition and selection of ions.

When changes occur in the voltage across a membrane, some channels are opened by electrical stimulus, or they may respond to chemicals, drugs or hormones.

Neurotransmitters, or may be activated by ligands. If there are changes in temperature or deformation by narrowing, widening of the membrane, they may be opened and mechanically.

Some ionic channels are opened or closed randomly regardless of the value of the membrane potential in which it is said that this "gating" is independent of voltage. However, certain ionic channels control membrane potential. When such channels are open, they can conduct electric current allowing ions to pass through the cytoplasmic membrane of the cell. These ions generate a current and establish an electromechanical gradient either positive or negative, depending charges on the ions, their quantity of direction, inward or outward, and the structure of the cytoplasmic membrane itself. Involved are different processes of activation, deactivation, inactivation, and finally reactivation.

Activation is the process of opening up the cell channels, responsive to the fact that the voltage within the cell membrane is more positive with respect to the outside. This is knows as depolarization.

Deactivation is the opposite process, which relates to the closing of a channel responsive to reversal of membrane potential.

Voltage of the interior of the membrane becoming more negative this is known as repolarization.

Inactivation relates to the closing of the channels during deactivation and occurs as the interior of the membrane is more positive. However, there is always a delay with respect to activation of a channel. As suggested above, a difference of voltage between the sides of a channel of a cell membrane causes the voltage gradient across said channels, also known as the current gate.

Some of these channels have a "refractory" aspect, also known as an inactive channel and is believed to be caused by an opening of a sub-unit of the channel.

The inventors believe that the flow of electrons or existence of the electrons of a voltage gradient for a longer time and, therefore, in a greater quantity, enhances activation, causing a greater exchange of ions and more effective control of membrane potential, enhancing intracellular currents from the stage of repolarization by giving them more time to the cell to react. See FIG. 7, as discussed below. One must also remember that the function of excitable cells depends on the entry of Na+ at an intensity of +61 mV, via Na channels, when activated. This entry of Na+ produces a depolarization of the membrane potential, facilitating the opening of more channels to the Na+ potential for 1-2 milliseconds. When at rest the cells of Na+ ions cause little opening and therefore cause inactivation of the Na channels.

The proteins associated with the extracellular K+ channels cause depolarization, that is, these channels are facilitated by the output of K+ ion about 90 Mv of the cell which contributes to the polarization of the membrane potential, and its rest potential of 90MV this activity automatically triggers the cells and helps the release of neurotransmitters, insulin secretion, cell control of membrane potential.

Excitability, transportation of electrolyte and muscle contraction affect regulation of cell volume as do the channels of Na+. There exist K+ channels, which influence the membrane potential and causes potential of rest and regulation of the volume of intracellular liquid. These channels can be similarly modified as to the time and the quantity of the flow of electrons effected by the inventive treatment including variables of frequency, pulse, wavelength of applied stimulation.

In resting cells, the intracellular concentration of Ca2+ is 20,000 times less at rest than outside. That is Ca2+ is too low but is permeable with activation.

The membrane potential caused by the output of the K+ and its reactivation of channels produces a repolarization of the membrane, thus obtaining an input of Ca2+ for each K+ that exists out of the cell.

Intracellular Ca2+ is important in many biological processes including the potential for action, duration of action, excitability and contraction, release of neuro-transmitters, release or hormones, release of growth factors, synaptogenesis, osteogenesis, process of cell differentiation, hypertrophy, remodeling and increase of the release of insulin to the beta cells of the islets of the pancreas, including the breaking of the intracellular vesicles that there are stored with insulin. Process our treatment is largely based on this process.

Other important channels are those of calcium also regulate cellular excitability and its transmembrane by regulating the cellular pH and volume of influx.

One well-studied calcium dependent process is the secretion of neuro-transmitters at nerve terminals. See Hille, page 104 thereof. Within the presynaptic terminal of every chemical synapse, there are membrane-bounded vesicular-containing high concentrations of neurotransmitter molecules of various types. When such an action potential engages a neurotransmitter, the membranes having one or more of these vesicles in their surface membrane, release a group of neuro-transmitters into the cellular space. This is conceptually shown in FIG. 6. In the pancreas, there exist the above noted pancreatic acinar cells which contain zymogen granules which assist in cellular functions thereof.

Normally stimulated secretion from nerve terminals of most excitable cells require that the extracellular calcium anions $Ca^{2+}$ pass thru ionic channels of the cell. The above is shown at a cellular level in the schematic view of FIG. 7 which shows a calcium anion channel 58 of cell 60 as well as the egress of a potassium anion through a so-called KATP channel 62 when a calcium anion enters the cell. This process triggers a variety of functions which relate to insulin secretion. Lack of sufficient secretion is of course the primary cause of diabetes as it is broadly understood. FIG. 7 therefore illustrates the current model of insulin secretion (Ashcroft, "Ion Channels and Disease," 2000, p. 155).

In summary, FIG. 7 indicates, in a normal functioning of the beta cell, that when plasma glucose levels rise, glucose uptake and metabolism by the pancreatic beta cells is enhanced, producing an increase in the intracellular ATP which is the primary cellular energy source. These changes act in concert to close calcium channels 62 in the beta-cell membrane because ATP inhibits, whereas MgADP (shown in FIG. 3) activates, calcium ion channel activity. In that calcium channel activity determines the beta cell resting potential, its closure causes a membrane depolarization 64 that activates voltage-gated calcium anion channels 62, increasing calcium influx and stimulating insulin release. However, insufficient charge upon intracellular calcium may, it is believed, be one cause of inhibition of the above-described normal metabolic process of the pancreatic beta cells. In other words, if intracellular calcium, or its relevant neurotransmitters, lack sufficient charge, insufficient electrical energy 86 is provided to secretory granules 68 sufficient to effect insulin release 70, that is necessary to metabolize glucose 72.

Another view of insulin secretion is that, by blockage of potassium ion channels 62, sufficient charge can be sustained within the cell to maintain normal function of secretory granules 68 and therefore of insulin release 70. Therapeutic drugs which seek to so modulate insulin secretion by control of the potassium channels are sulphonylureaus and diazoxide.

In summary, when blood glucose 72 rises, the uptake thereof is increased by the action of the calcium anions $Ca^{2+}$ entering cell 60 through channels 38. Aspects of this metabolism cause the potassium ATP channels to close which results in membrane polarization 64, a change of voltage potential at calcium ion channels 58, and an increase in cytoplasmic anionic calcium that triggers the function of insulin secretory granules 68. It is therefore desirable to regulate calcium channel activity by maintaining a low level of blood glucose. But, this requires that an adequate molarity of $Ca^{2+}$ exist in the beta cells.

The relationships of the offset of ionic calcium on membrane potential of the cell, ionic current flow within the cell, and molarity of calcium within the cell are shown in FIGS. 8 and 9 respectively. FIG. 10 indicates that the percent of time of calcium channel opening as a function of membrane potential and calcium molarity within the intracellular media. Stated otherwise, an increase in membrane potential will increase the time that voltage-gated ionic channels of the cell are open. In view of the above, it appears an appropriate increase in ionic calcium within beta cells of the pancreas will bring about an increase in insulin release if supported by a sufficiency of the membrane potential. The cross-hatched area 74 at the top of the graph of FIG. 10 represents a confluence of parameters most beneficial to the health of the beta cells.

It is to be appreciated that the channels of K+ are dependent on the level of ATP and therefore of glucose in blood will be closed and the cell membrane is depolarized; with this, dependent Ca2+ channels of voltage are opened and the Ca2+ enters the cell. This increase in intracellular Ca2+ activation produces phospholipase that divides the phospholipids in the membrane phosphatidylinositol 1,4,5 triphosphate and diaclyglycerol. The inositol 1,4,5-triphosphate (IP3) to protein receptors on the membrane of the endoplasmic reticulum allow the release of the Ca2+ (ER) via the channels increasing the intracellular concentrations of Ca2+.

These amounts of Ca2+ increased are responsible for causing activation of the synaptotagmin, which helps to release insulin previously stored in the vesicles. With this being the main mechanism for the release of insulin.

Other substances induce the release of the hormone, amino acids, acetylcholine, which is released from the stimulation of the terminations of the vagus nerve (30). Our treatment stimulates the paraverterbral ganglia and the superior mesenteric ganglion 40 (see FIG. 3) which stimulate enteroendrocrine cells of the intestinal mucosa by freeing cholecystokinin that acts to release insulin. There are three amino acids, lysine, glycine, and arginine that act with the same mechanism from glucose in the blood, all of which activate the cellular membrane potential, that is, increase the permeability of ionic channels in the beta cells and produce an increase in insulin release. The autonomic nervous system (ANS), as above noted, controls involuntary action, receives information from visceral parts of the brain, and the internal environment, to act on the muscles, glands, and blood vessels, is an efferent system (see FIG. 3), transmitting impulses from the CNS up to the periphery's stimulating many peripheral elements.

We have seen the activation of ion channels by voltage gradients, but there are other controls of membrane potential.

Other means of activations of ion channels include, for example, the ligands, which are produced by the interaction of neurotransmitters and hormones, with a portion of the channel receptor, which causes a cascade of enzymatic events and phosphorylation, all of which produce the necessary energy to keep the channels open or closed, as needed. Enabling receptors are located inside and outside of layers of the membrane and according to the electrical charges of proteins (positive or negative), depending on the existing gradient at a given channel.

There are channels which are regulated by mechanical action that are directed by Pacinian corpuscles (PC). Such membranes open by stretching and/or contraction.

As a conclusion to the above, we see that the ionic channels occur in a wide variety of biological processes which require rapid changes in the cell, for example: Heart muscle contraction, transport of ions and nutrients through the epithelium, and T lymphocyte control of membrane Activation and release of insulin by the beta cells of the Islets of the pancreas comprises our key objectives in the search for new methods and/or treatments to improve and to cure a number of pathological processes.

As in Type II Diabetes Mellitus (T2D) ions passing through the cytoplasmic membrane for their normal metabolism have been discovered to exist in all human cells, functioning as a "biological clock." Researchers from the University of California, at Irvine have reported important findings in day/night cycles and its relationship to metabolism and cellular energy, and have also suggested new treatments for cancer, obesity, and other diseases. Such circadian rhythms of 24 hours govern or direct fundamental physiological functions in almost all living organisms.

Sassone-Corsi discovered the relationship of proteins to a "protein clock" that modulates energy levels involved in the metabolism, equilibrium, and cellular aging. An imbalance in this process can cause disease. And other imbalances and therefore stimulus can induce lead or lag in the biological clock using effects of pulsed light and darkness during a 24-hour period to thus influence hormonal secretions of the glands in range of one to two hours, resulting in a system of internal regulation of the time. As such, nutritional factors, environment, and cycles of light/dark all influence the life of the cell and therefore the organism. This organization of time is altered in many pathophysiological conditions such an aging and endocrine diseases.

Researchers (the neuroscientist at the Cambridge University, Dr. Akhelesh Reddy) discovered a circadian oscillator in mammals located in suprachiasmatic nucleus 76 of the anterior hypothalamus 78 provides information of the physiological processes of the body, the operation of which is genetically pre-programmed. See FIG. 11. This postulates the necessity of a stable biological clock for healthy living in the early hours of the morning and considered ideal for work of concentration, the afternoon for manual work, and until the end of the afternoon for the proactive of sports where more energy is released by the cell. That is why our treatment, as below described, must be applied after 11:00 a.m. and before 8:00 p.m.

The period since about 1983 has witnessed a dramatic increase in the prevalence in patients of a cluster of inter-related metabolic disease stages, primarily caused by obesity and immune disease stages, jeopardizing homeostasis and leading to the diabetic state. The incidence of diabetes, with or without obesity, has reached epidemic proportions, bringing with it impaired quality of life and life span due to serious clinical co-morbidities such as peripheral vascular and neuropathic disease, with or without pain, ulcerative skin lesions often leading to infection, gangrene, and amputation, vision loss, cardiac and renal failure and brain disorders. Without question, chronic disease associated with diabetes represents a heavy and growing burden to society in terms of both direct healthcare costs that have reached catastrophic levels and mortality rates (American Health Rankings, 2010 edition).

According to American Diabetes Association, as of 2010, 23.6 million children and adults, approximately 8% of population in the United States (US), have diabetes, and over 57 million people are clinically considered pre-diabetic in the US. According to United HealthCare, based on current trends, 52% of the US adult population could have pre-diabetes or diabetes by 2020—up from an estimated 40% in 2010, resulting in costs estimated at $3.4 trillion for diabetes-related care over the decade from 2010 to 2020. The incident of Type 2 diabetes (T2D) in adolescents has increased 10 fold from 1982 to 1994 (Pinhas-Hamiel 1996). Over 25% of obese children are considered glucose intolerant. Insulin resistance is related to inflammation and obesity induces a stage of chronic inflammation. In obese stages, adipose tissue secretes inflammatory agents such as cytokines. Adipose tissue macrophages adversely alter insulin sensitivity in animal models. Obesity can be reframed as an inflammatory disease, with macrophages acting at the junction between over nutrition and inflammation.

Provided herein are methods, systems and apparatuses for preserving, restoring or affecting pancreatic beta cell function in a subject. These methods include electrically stimulating C-afferent sensory nerve fibers innervating pancreatic beta cells but originating in the spinal cord in a subject, in which the electrical stimulation modulates a secretion of calcitonin gene-related peptide (CGRP) from the C-afferent sensory nerve fibers (see FIG. 3); determining a level of a biomarker in the subject and repeating the electrical stimulation as a function of the level of the biomarker.

With respect to the prior art as is know to the within applicants, U.S. Patent Application Publication US2002/00026141 (2002) to Houben et al, teaches a system for pancreatic stimulation and glucose measurement. Houben relates to an implantable insulin pump and, as such, is representative of various implantable or other insulin pumps which have been suggested over the last 40 years. The system, as disclosed herein, is not implantable and operates strictly through neurophysiologic stimulation to the spine and associated areas.

U.S. Pat. No. 4,477,944 (2009) to Whitehurst et al, teaches Methods and Systems for Modulation of Pancreatic Endocrine Secretion and Treatment of Diabetes. It, like Houben, is an implantable system, and, as such, simply reflects an improvement of Houben.

U.S. Patent Application Publication US2011/0230939 (2011) to Weinstock, teaches a system for diagnosis and treatment of diabetes. The system of Weinstock, while not implantable, does not make use of the same neurophysiologic waveforms or treatment strategy as is taught by the within invention.

WIPO Publication No. WO 2012/083259 to Perryman teaches a Method, System and Apparatus for Control of Pancreatic Cell Function to Improve Insulin Production. Perryman teaches a method of nerve innervation of the pancreas which includes an implantable system but also purports to teach a non-implantable system. However, the bioelectric method of the nerve stimulation of the pancreas of Perryman bears no relationship to that taught by the instant invention.

SUMMARY OF THE INVENTION

The present invention includes an electromagnetic asymmetric biphasic therapeutic waveform used in neurophysiologic treatment of conditions associated with the opening and closing of ionic and other channels associated with beta cells of the pancreas. The waveform includes a positive part having a pulse width in a range of 40 to 60 milliseconds, and a positively pointing segment along a top portion of said part. The waveform further includes a negative spike-like aspect which drops sharply negatively following said positive portion at an interface between said positive and negative parts. The negative drop of voltage at said interface is in a range of 75 to 90 percent of the entire peak-to-peak voltage of the entirety of said waveform, in which such entire peak-to-peak voltage defines a range of about 10 to about 100 volts AC. The negative spike-like first aspect of said negative part exhibits a pulse width in the range of 40 to 60 milliseconds but, thereafter, approaches a neutral voltage level of said waveform in a gradual asymptotic manner. Said first aspect of said negative part of the waveform is followed by a second aspect which more slowly but asymptotically approaches said neutral level over a period in a range of 100 to 200 milliseconds, this prior to the initiation of the next waveform. The current of said waveform defines a range of about 300 to about 1000 micro amps.

An object of the invention is to provide a waveform having particular utility in the neurophysiologic stimulation of nerves innervating the pancreas.

Another object is to provide a method for the treatment of diabetes which uses said waveform.

It is a further object of the invention to provide a system, inclusive of a novel circuit and neurophysiologic stimulator, for the practice of the above method.

It is a yet further object to provide a method and system of the above type by which the nerves innervating the pancreas and its beta cells are reached by such waveform through the vagus nerve, celiac ganglia, and associated complexes.

It is a still further object of the invention to provide a method, system and apparatus of the above type, by which the inventive waveform facilitates an extended period of opening and functionality of the ionic and other channels of the membranes of beta cells of the pancreas, thereby providing nutrients and membrane potential thereto.

The above and yet other objects and advantages of the above invention will become apparent from the hereinafter set forth Brief Description of the Drawings, Detailed Description of the Invention, and Claims appended herewith.

DEFINITIONS USED HEREIN

Figure 1:
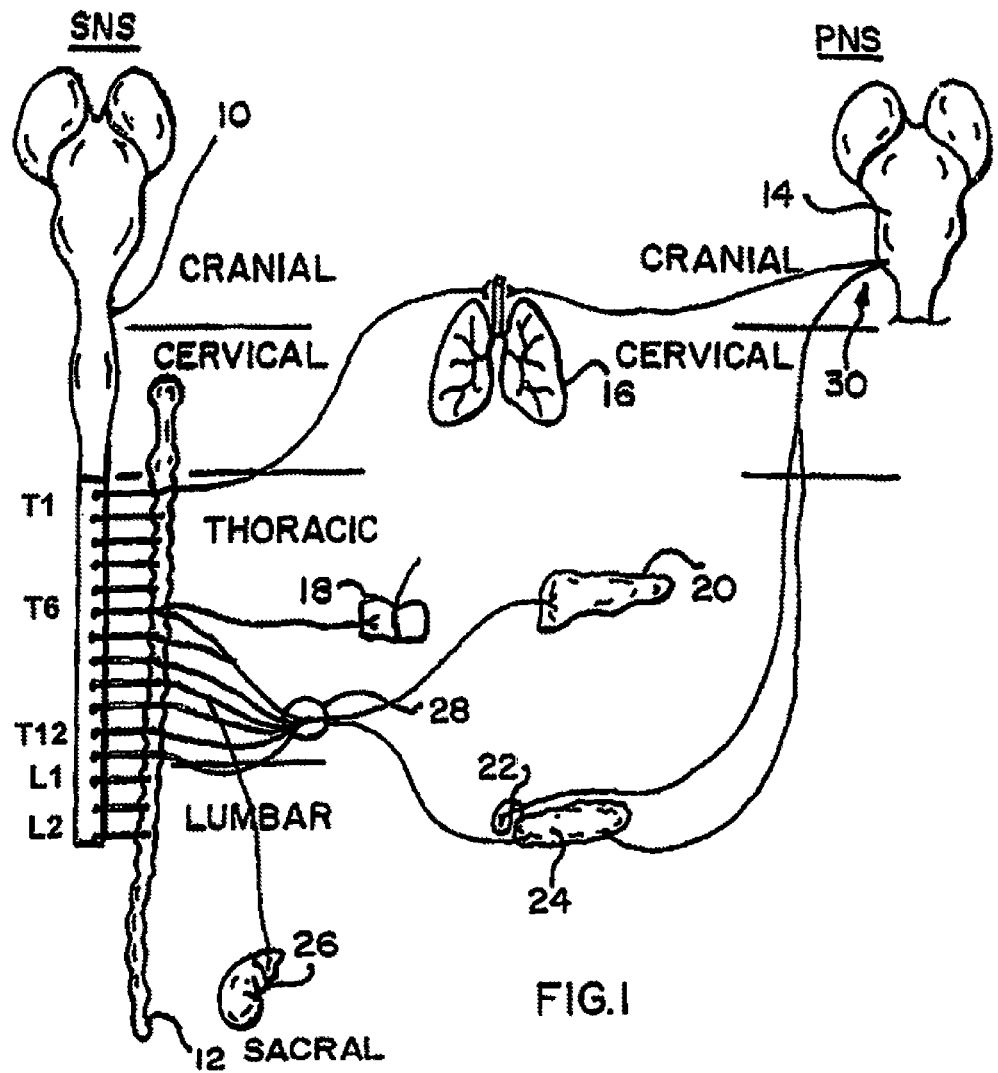
FIG. 1 is a schematic anatomical view of the sympathetic nervous system and parasympathetic nervous system and organs associated therewith.

"Biomarker" means any physiological indicating species produced by a subject. Examples of biomarkers include, but are not limited to, insulin, glucose, abdominal skin blood flow, abdominal skin temperature, and abdominal muscle electrical activity.

"C-afferent sensory nerve fibers" means unmyelinated postganglionic fibers of the autonomic nervous system, also the unmyelinated fibers at the dorsal roots and at free nerve endings, that convey sensory impulses from the periphery to the central nervous system. See FIG. 3.

"Diabetes mellitus" means diabetic states that include T1D, T2D and gestational diabetes.

"Dorsal root or dorsal root entry zone" means the posterior root that is an afferent sensory root of a spinal nerve.

"Dorsal ganglia" means the nerve structure at the distal end of the dorsal root, which contains the neuron cell bodies of the nerve fibers conveyed by the root.

"Electrical stimulation" means the application of the nerve waveform to stimulate nerves in communication with the pancreas.

"Electrode" means an electrical conductor used to make contact with the skin of a patient. An electrode can be an anode or a cathode. An electrode pair means two electrodes: one anode and one cathode.

"Impaired glucose tolerance (IGT)" means a pre-diabetic state of dysglycemia that is associated with insulin resistance and increased risk of cardiovascular pathology.

"Lifestyle change" means changes in diet, exercise, nutraceutical and pharmaceutical regimens.

"Pancreatic beta cells" means insulin-producing cells situated in the Islets of Langerhans.

"Peripheral nerves" means nerves and ganglia outside of the brain and spinal cord.

"Pre-diabetic" means a condition thought to be a precursor of adult-onset diabetes mellitus, marked by carbohydrate intolerance or other symptoms of the disease.

"Spinal nerve bundles" means nerves within the spinal cord that are grouped together.

"Type 1 diabetes (T1D)" means a condition characterized by loss of the insulin-producing beta cells of the Islets of Langerhans in the pancreas leading to insulin deficiency. This type of diabetes can be further classified as immune-mediated or idiopathic. Type 1 diabetes can affect children or adults but was traditionally termed "juvenile diabetes" because it represents a majority of the diabetes cases in children.

"Type II diabetes (T2D)" means a condition characterized by insulin resistance which may be combined with relatively reduced insulin secretion.

DETAILED DESCRIPTION OF THE INVENTION

The beta cell is a type of cell in the pancreas located in the Islets of Langerhans, its main function being to synthesize and secrete the hormone insulin that is the one that controls the quantities of glucose circulating in blood. The cells normally produce the hormone and are released daily at about 40 to 50 Units. The Islets also have several hundred of these cells. Insulin is stored and available in vesicles within the cytoplasm of these cells, and is secreted when needed. If some beta cells are affected, that is, if only between 10% and 20% remain in good condition, the symptoms of diabetes will be displayed. TD2 occurs with more frequency than TD1, and happens in people after 40 years although pre-teens with obesity may encounter TD2. In this type of diabetes, the ability to produce insulin doesn't disappear but the cells of the body offer resistance to the action of the hormone.

The beta cells of the Islets of Langerhans release insulin in two phases:

A. Quick response to increased levels of glucose in the blood.

B. Sustained-release and slowly due to rupture of the vesicles that carry stored insulin. This effect is independent of the quantity of circulating glucose in the blood.

Beta cells need a fundamental energy to perform their functions. Glucose generally penetrates through membrane channels, causing GLUT 212 glycolysis production inside the cytoplasm in the respiratory cycle, formed by oxidation, which includes several molecules of ATP for high energy levels. See FIG. 7 and description thereof.

Figure 12:
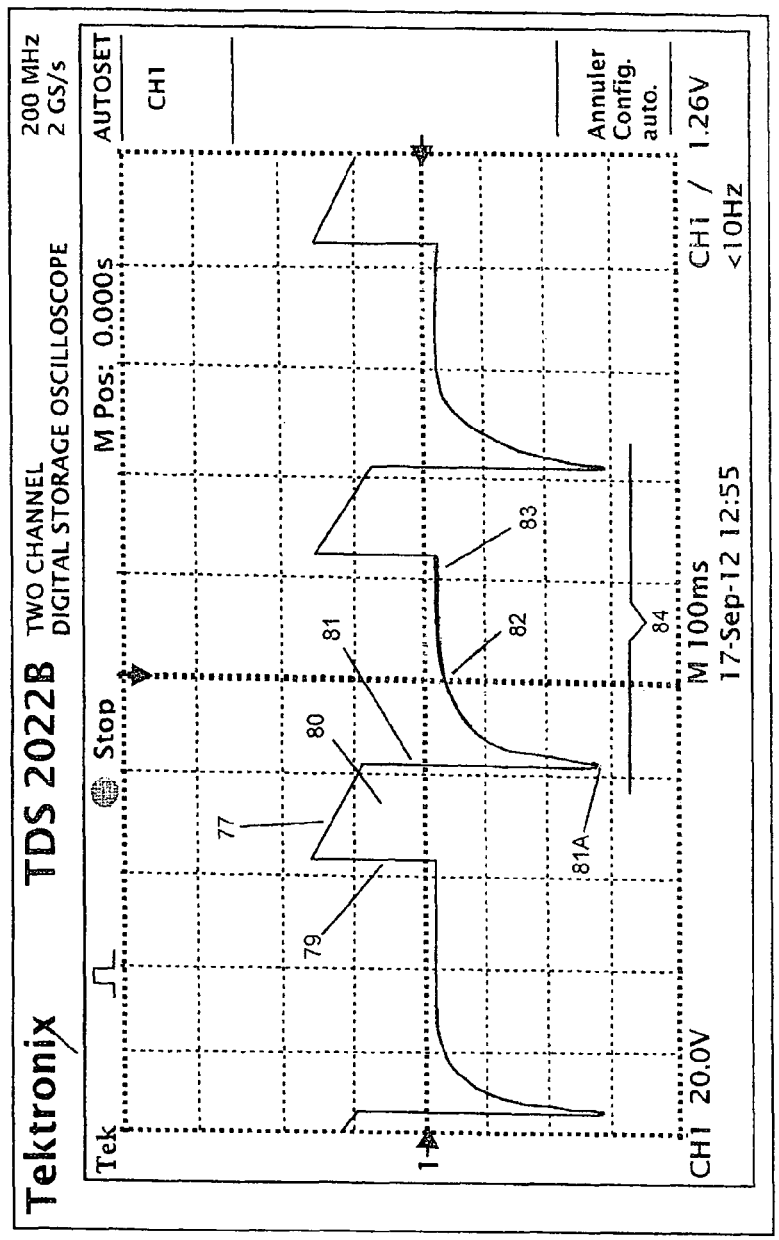
FIG. 12 is an oscillation screen shot of the inventive electro therapeutic waveform.

With respect to FIG. 12, there is shown a novel electromagnetic waveform which is employed in the present method of delivery of neurophysiologic stimulation to nerves innervating the beta cells of the pancreas. As above descried, the malfunctioning of these cells is understood to be due to a failure of ionic and other channels of the beta cell membrane to open and close in response to essential ionic nutrients and other conditions which are external to the cytoplasm. While the methodology of use associated with waveforms of FIG. 12, as described herein, is set forth below, an understanding the waveform itself is important to an understanding of the inventive method and system herein. That is, in FIG. 12 it may be seen that an overall waveform 84 includes a positive portion 80 and a negative portion 82. Therein, the positive portion is relatively simple, that is, it consists of a vertical upward step 79 followed by a downward slope 77 which in turn is followed by a long sharp downward drop 81 which ends in a negatively directed point 81A. Therefrom, the waveform begins an asymptotic return 82 toward the negative or zero voltage level. The negative pulse aspect, in its early stage, is the same in time as the pulse width of positive part 80 of the waveform, that is, in a range of 40 to 60 milliseconds with 50 milliseconds of each being preferable. Following the first part of the negative aspect, waveform 82 is an extended gradual asymptotic approach of a second aspect 83 of the waveform 84. The second part or tail of the negative portion of the waveform is longer than that of the initial portion and, typically, can have a period in the range of about 100 to about 200 milliseconds, with 153 milliseconds representing the preferred embodiment. Accordingly, entire length of the first part of the negative portion starting at point 81A and added to the second portion 83 creates a total of about 206 milliseconds for the entire negative portion 82 of the waveform which, when added to the 50 millisecond pulse width of the positive portion, yields an aggregate wave length of about 256 milliseconds in a preferred embodiment.

Figure 5:
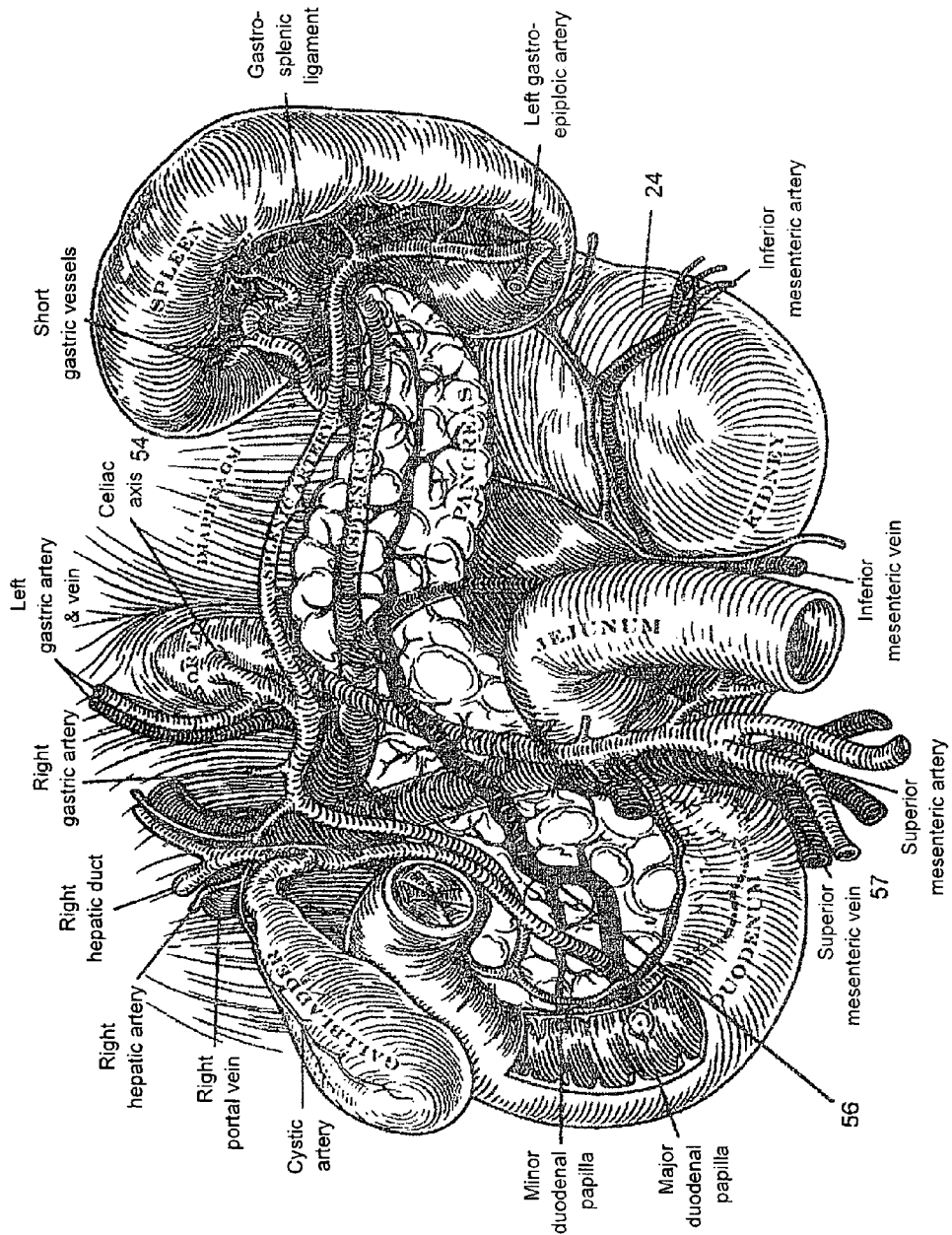
FIG. 5 is an anatomic schematic view of the pancreas and nerves organs surrounding it.
Figure 6:
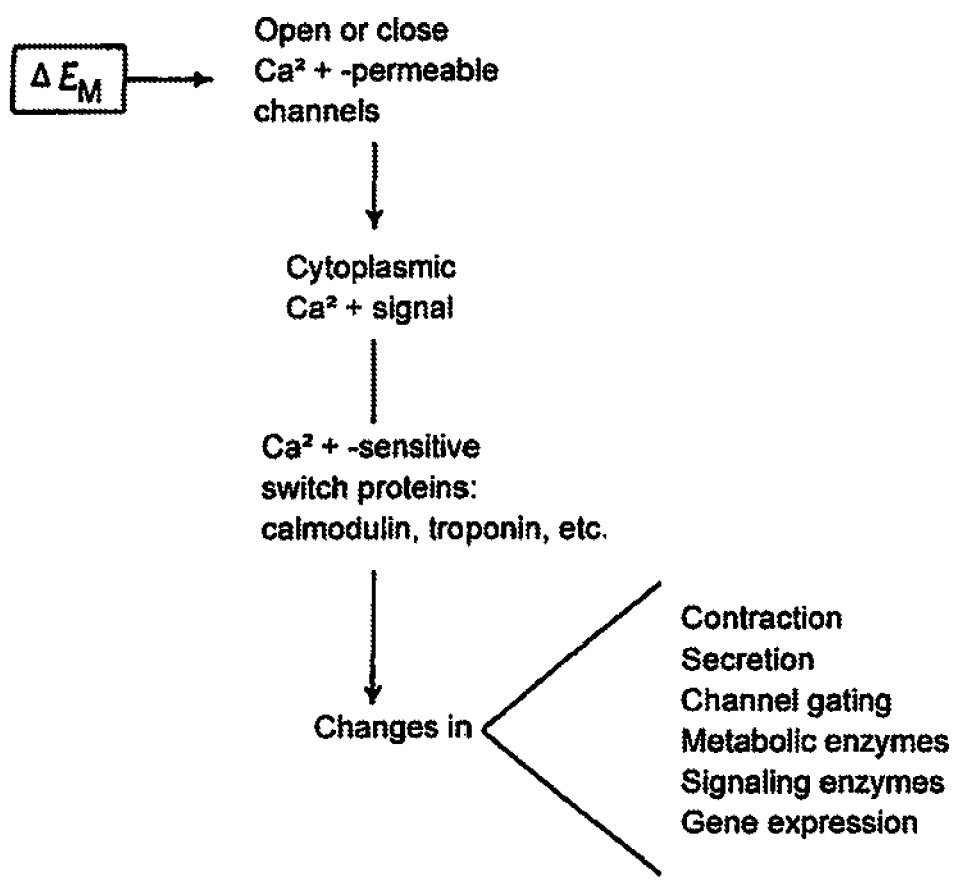
FIG. 6 is a flow diagram showing the flow of calcium and other changes that occur when membrane potential changes are sensed by a cell.

As is more fully described below, the primary electromagnetic physiologic function of the positive portion 80 of the waveform 84 is to project the electron content of the waveform through the vagus and celiac complexes of the nervous system, thereby reaching the pancreas and its beta cells through at least celiac axis 54, pancreatic duct 56, and superior mesenteric 57, shown in FIG. 5, this in addition to other mechanisms by which said waveform is delivered, as is more fully set forth below.

In general, it is the positive portion 80 of the waveform that provides inertia or impetus for the movement of the waveform through the nervous system, in accordance with the method below-described, while it is the negative portion 82, largely facilitated by capacitor C3 described below with reference to FIG. 13, which provides the unique benefits of the present system of extending the duration that the positive portion 80 of the waveform will operate to open, normalize or re-polarize the ionic and other channels of the membranes of the beta cells of the pancreas.

The waveform employed may be termed a variable, asymmetric, biphasic wave having an amplitude in the range of 10 to 100 volts AC. This wave however notwithstanding its high potential is in the range of a low amperage, that is, on the order of 70 micro-amperes. However, what is most salient about the waveform shown in FIG. 12 is its particular geometry, that is, its biphasic geometry. As above noted, the wave has two portions, namely, said positive portion 80 having a positive pulse width of about 50 milliseconds and the negative portion 82 having a total pulse width of about 156 milliseconds. However, it is the unique shape of the positive and negative portions 80 and 82 respectively of the inventive waveform, which is germane to the function of the inventive method.

As is more fully described above, positive portion 80 and its sharp region 77 is enabled by positive step 79 which operates as a driver or spike which imparts electrons of the desired pulse width, amplitude, current and power throughout the nervous system to the ultimately intended organ, that is, the pancreas and the beta cells thereof, whereas the negative or capacitative portion 82, including its negative spike 81A and long tail 83 of the waveform 84, have, as their primary function, the extension of the period during which ionic and other cellular channels, as above described, are kept open, permitting a longer period of inflow or outflow (as the case may be with respect to a particular cellular component), thereby enhancing the effectiveness of the waveform over prior art efforts concerning the treatment of diabetes by electrical or electro physical means. The total duration of portion 80 and portion 82 of waveform 84 is preferably 256 milliseconds, which equates to 3.9 Hertz. A range of between 3 and 5 Hertz has been found to be effective for given patients and, as such, it is to be understood that the total pulse width of wave 84 may therefore fall in the range of about 200 to about 335 milliseconds with the time ratio between the capacitative part 82 and the positive rectangular-like portion 80 of the waveform typically being about 3:1. For example, if the entire wave 84 is 333 milliseconds, part 80 will be about 83 milliseconds and the negative capacitive part 82 would be about 250 milliseconds. If the positive part is 50 ms, the negative part will be 206 ms.

It is noted that the preferred frequency of 3.9 Hertz (corresponding to an aggregate pulse width of 256 milliseconds) corresponds generally to three times the beat rate of the human heart when at rest. Thus, the heart at rest normally beats at 1.666 times per second. As such, 3.9 Hertz represents three reiterations of biphasic wave 84 for each beat of the human heart.

Figure 13:
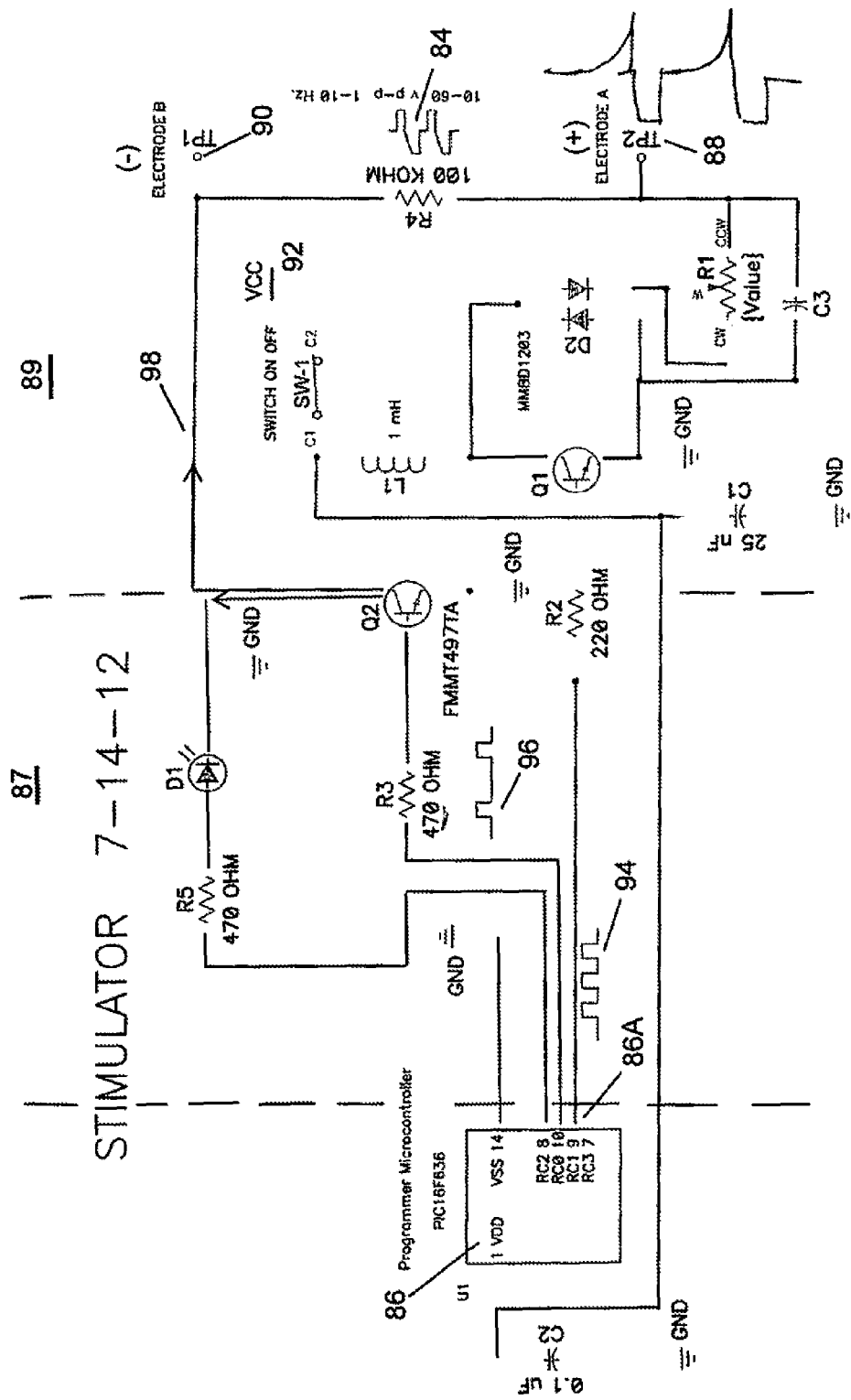
FIG. 13 is an electrical schematic used in the generation of the waveform of FIG. 12.
Figure 14:
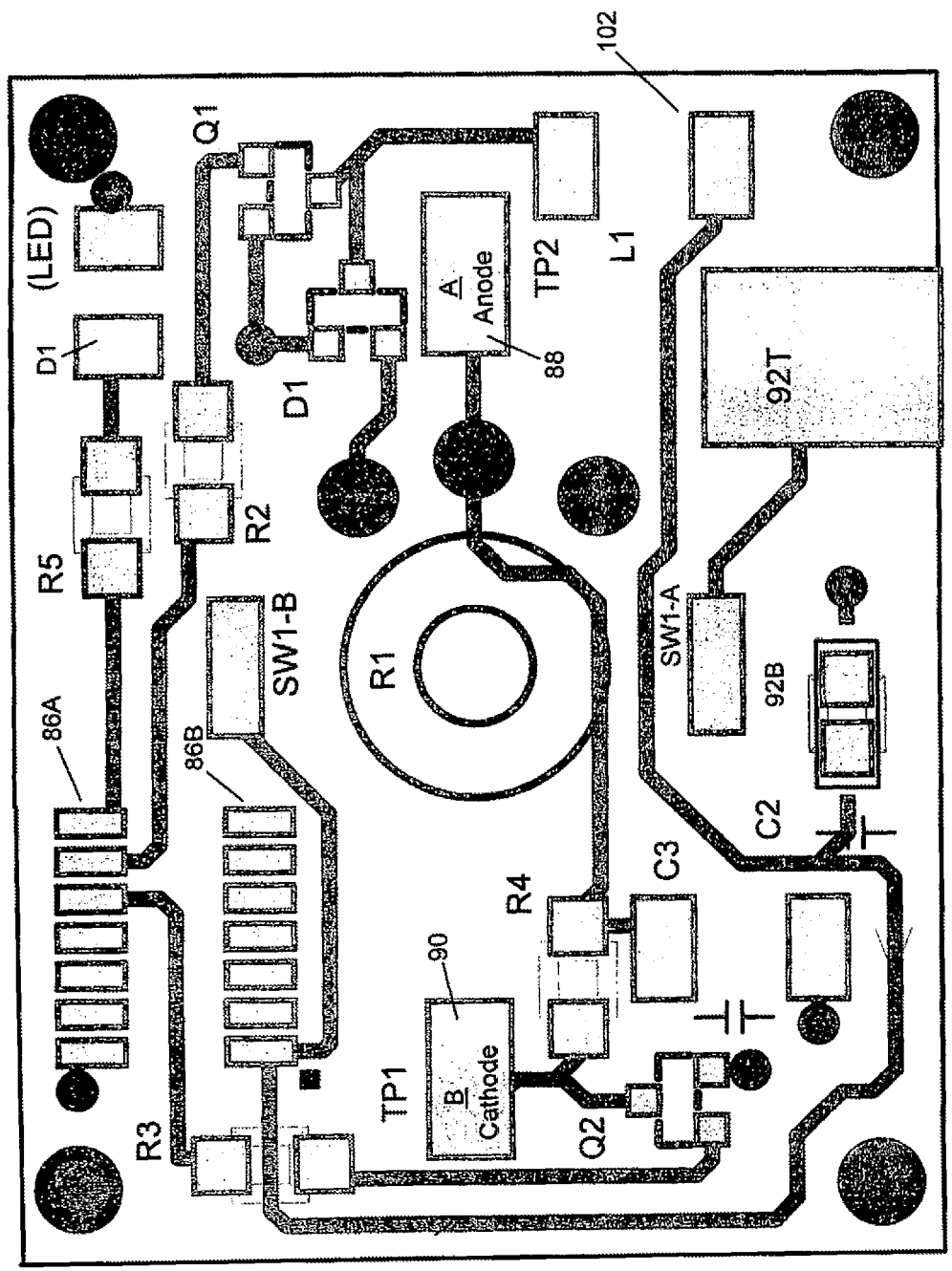
FIG. 14 is an integrated circuit board layout of the electrical schematic of FIG. 13.
Figure 15:
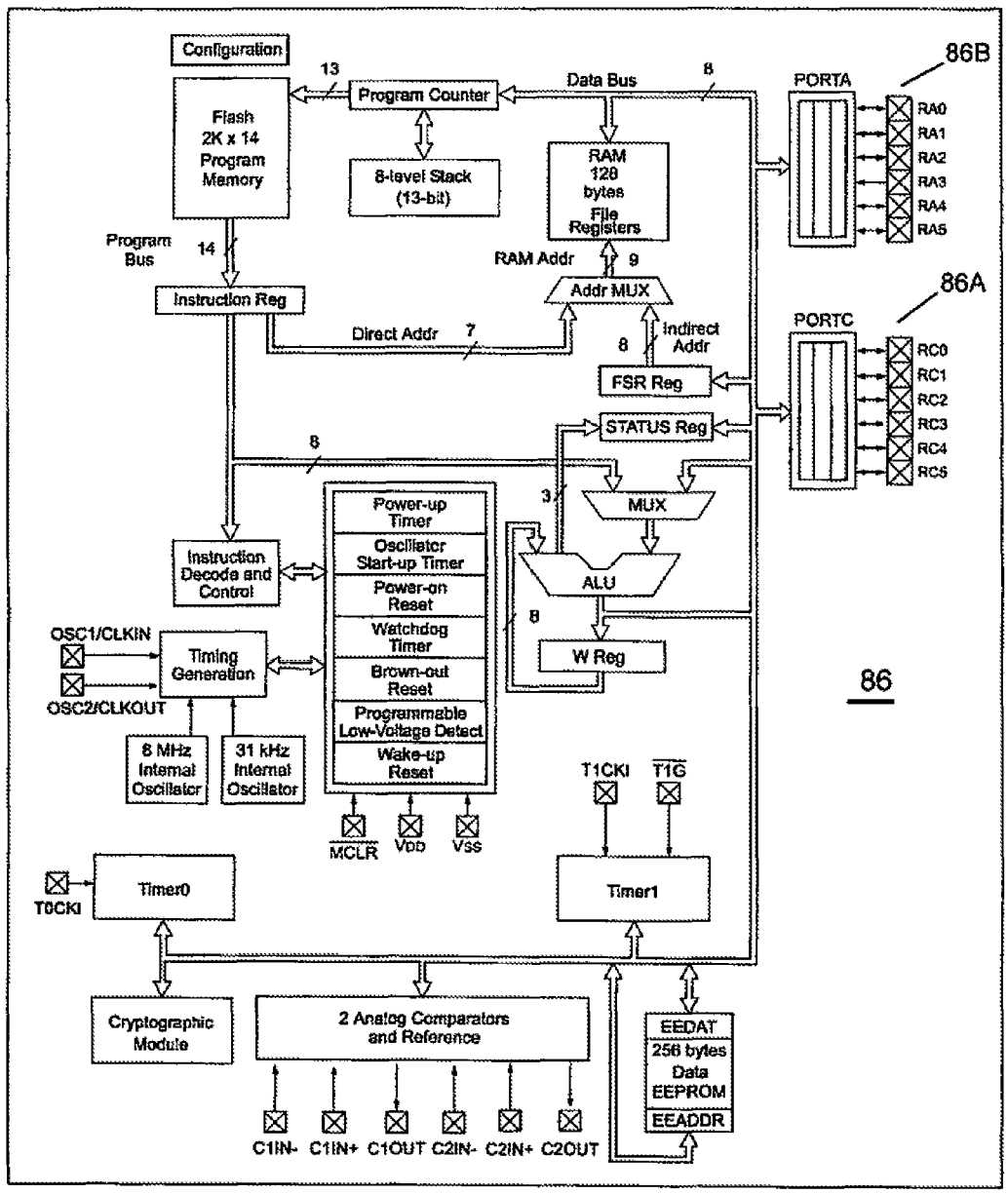
FIG. 15 is a block diagrammatic view of the microprocessor used in the circuits of FIGS. 13 and 14.

The waveform above-described may be accomplished through various circuitry but an example thereof is shown in FIGS. 13-15 in which, more particularly, FIG. 13 is a conventional circuit diagram, FIG. 14 is a circuit board schematic of the conventional circuit diagram of FIG. 13, and FIG. 15 is a block diagram of micro processor 86 shown in FIGS. 13 and 14. The system also includes a novel arrangement of treatment electrodes as are more fully described with respect to FIGS. 16 and 17. These electrodes include are electrode A (anode) 88 and electrode B (cathode) 90 in the circuit diagrams of FIGS. 13 and 14. In electrical terms, these electrodes are isolated from any ground (GND in FIG. 13) associated with the system so that the integrity of waveform 84 may at all times be maintained.

The circuit shown in FIG. 13 may be operated off of a three-volt DC Ultralife cell battery U10004, having a voltage range of 1.5 to 3.3 VDC. Said battery is indicated, as to the top thereof, as element 92T in FIG. 15 and as to the bottom thereof as element 92B in FIG. 15 and simply as 92 or VCC in FIG. 13. Microcontroller 86 exhibits two groups of outputs as may be noted in FIGS. 14 and 15 indicated as 86A and 86B in FIGS. 14 and 15. As may be noted in FIG. 13, the most important set of ports of microcontroller 86 is port 86B, since it leads into wave establishing circuit 87. An originally generated pulse therein 94 is shown in FIG. 13 coming off of port 86B of the microcontroller. Associated therewith is resistor R2 shown in FIGS. 13 and 14. The waveform 94 is modified to waveform 96 (shown in FIG. 13) by the microcontroller 86 which is pre-programmed to provide a pulse train of an amplitude and frequency usable by part 87 of the present circuit. Coming off of port 86A of the microcontroller is also resistor R3 which provides a biasing function with respect to the base of transistor Q2. It operates in combination with diode D1 as an on-off LED for the system, while a switch, labeled SW1-B in FIG. 15, is connected to port 86B as a system on-off switch.

In general, the function of portion 87 of the circuit containing transistor Q2 is simply that of amplifying input pulse train 94 and modifying its frequency as is indicated by pulse train 96. That is, the essential formation and modification of pulse trains 94 and 96 occurs in the circuit port 87 with transistor Q2 shown at the middle of FIG. 13 and left of FIG. 14. The treatment part 89 of the circuit may be turned on or off by switch SW1, however the flow of energy between inductive and capacitative states within waveform 84 is governed by inductor L1, having typically a value of 1 MilliHenry, and C3 having, typically, a value of about 0.05 milliFarads and controlled by transistor Q1. More particularly, pulse train 96 feeds into the treatment part 89 of the circuit at path 98 and therefrom passes through resistor R4 (typically 100 ohms), said capacitor C3, said transistor Q1, and said inductor L1. Diode D2 indicates whether or not the treatment portion of the circuit is functioning.

Figure 11:
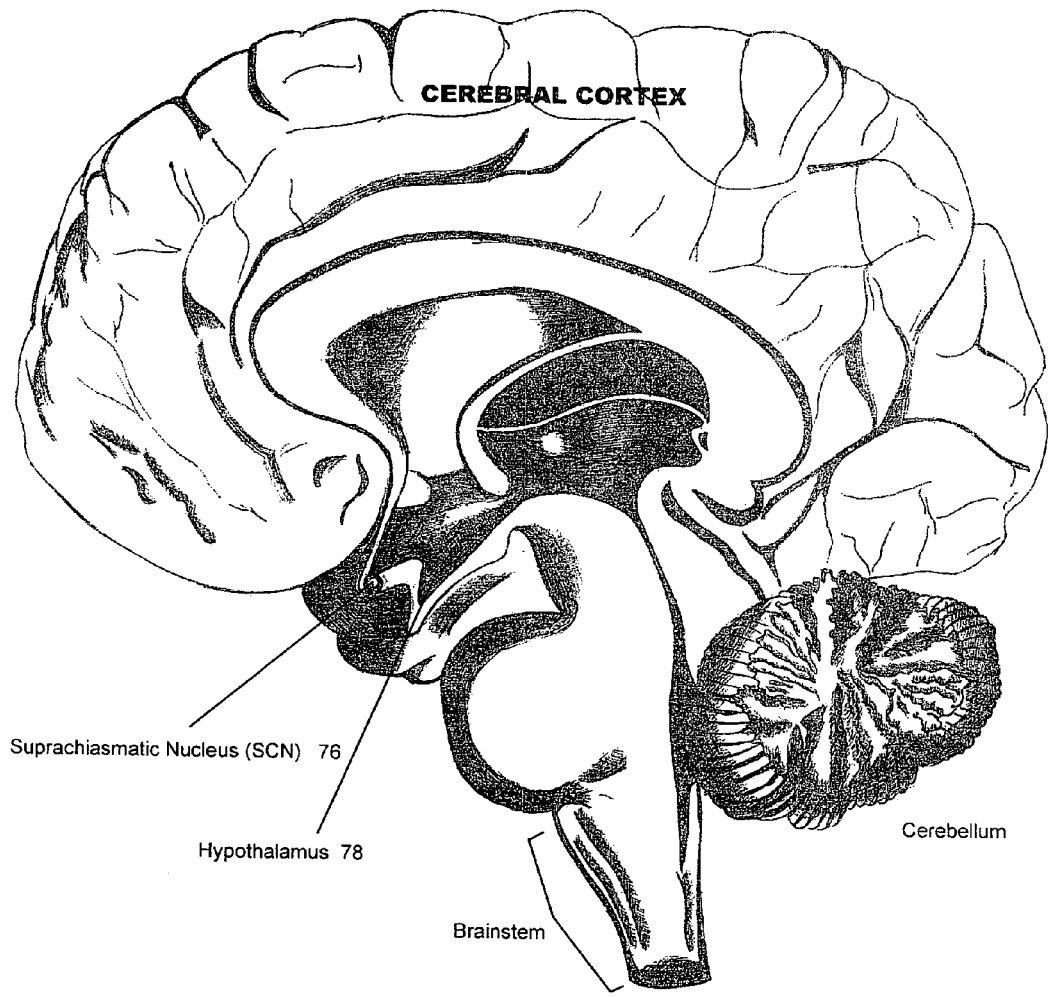
FIG. 11 is an anatomical view of the human brain.

The amplitude, that is, peak-to-peak amplitude of waveform 84 shown in FIGS. 11, 12 and 13 is controlled by the potentiometer as R1 in FIGS. 13 and 14. With the potentiometer, a voltage from substantially zero to about 100 volts may be obtained, with 70 volts peak-to-peak representing a generally used amplitude, that is, +35V positive and −35V negative. It is further noted that inductor L1 is primarily responsible for the geometry of positive portion 80 of wave 84 form and capacitor C3 is primarily responsible for the slow asymptotic decay geometry of portion 82 of waveform 84. The control of these, inclusive of their duration, is effected by transistor Q1 in combination with resistor R4, which also operates to bias the electrodes. As may be further noted, to the right of FIG. 13, the potentiometer R1 and resistor R4 provide their waveform 84 output to anode 88 which, as is more fully described below, is then passed through the treatment site at the cathode 90.

It is noted that capacitor C1 and C2 simply provide a noise filter function, so as to ensure the integrity of pulse trains 94 and 96 within the circuit as above described.

Figure 16:
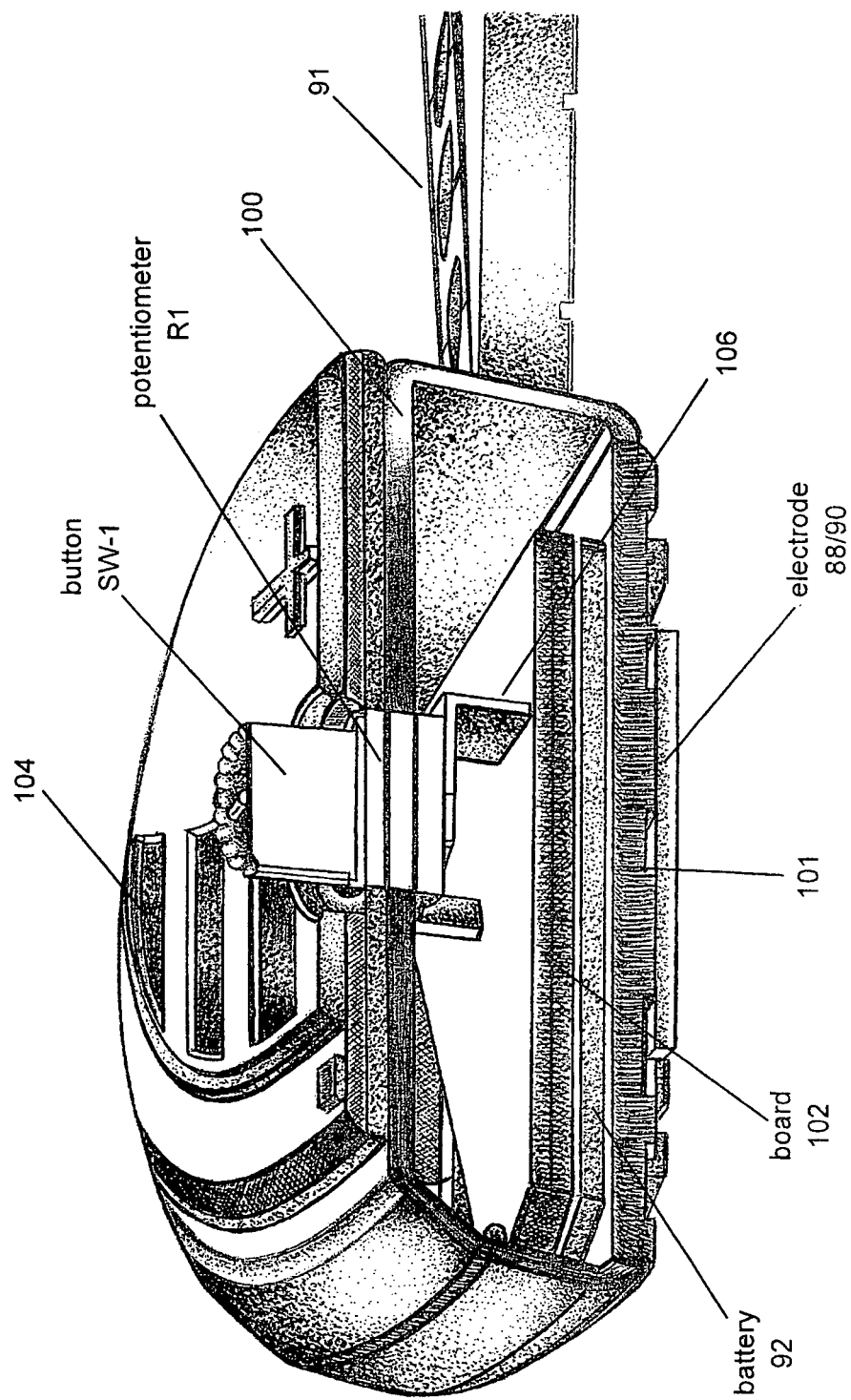
FIG. 16 is a diametric cross-sectional view of an electrode used in connection with the circuit of FIG. 14.

Shown in FIG. 16 is a representative arrangement within an electrode housing 100 of the features above-described. That is, within housing 100 is shown electrode 88 or 90, treatment pad 101, battery 92, and integrated circuit board 102. Further shown is potentiometer R1 and on-off button SW1 for the electrodes. Within housing 100 are openings 104 to provide for sufficient cooling of the IC board 102 which, typically, is offset from potentiometer R1 by a bracket 106.

In regards to FIGS. 13 and 14, are shown two different forms of diagrams of the same circuitry. Each of these circuits are essentially divided into three areas, namely, microcontroller portion at left of FIG. 13, shown in greater detail in FIG. 15, general pulse train forming portion 87 of the circuit and waveform or pulse train shaping 89 of the circuit. With respect to microcontroller 86, this consists of a first port 86A and a second port 86B (see also FIG. 15). As may be noted in section 87 of the circuit as shown in FIG. 13, the present invention operates primarily off of ports 86A of the microcontroller and, as may be noted, therefrom, an initial pulse of width 94 is generated off of pin RC1-9, while pins RC0-10 and RC2-8 of port 86A is connected to the primary pulse train generating circuit shown at the middle of FIG. 13, which consists of transistor 22 which is biased by resistor R3. The forms of the resultant amplified and slightly modified as to frequency pulse train is shown at 96 in FIG. 13. Diode D1 illuminates to show that the system is on while resistor R5 serves to properly bias diode D1 relative to ground.

The functions of the capacitors C1 in part 89 of the circuit and C2 in part 86 of the circuit is simply that of noise filters in order to assure the integrity of shape of all pulse trains employed in and generated by the present system. The output of transistor 22 may be seen to feed into line 98 of the circuits of FIGS. 13 and 14. The resultant output of waveform 84, above described, with regard to FIG. 12, is shown conceptually to the right of FIG. 13. However, its particular shaping is a result of a continual oscillation of energy between inductor L1 which may be at one milliHenry and capacitor C3 which may be at about 0.05 milliFarads. This oscillation of energy is modulated by transistor Q1 in which the amplitude of the ultimately formed output wave is controlled by potentiometer R1. In other words, the amplitude of the wave shown in FIG. 12 may be controlled from a relatively small to a considerable value as much as, for example, 100 volts peak, but preferably about 70 volts peak-to-peak. Although it is to be appreciated that microcontroller 86 at its input is powered by battery 92 which may be a three-volt DC lithium cell battery. As such, it is to be understood that the total power of the output waveform shown in FIG. 12, although much greater in terms of peak-to-peak voltage cannot exceed the power of the three volt DC battery which powers the entire system. All of part 80 of the circuit of FIG. 13 may be turned on or off by switch SW1 shown in FIGS. 13 and 14.

FIG. 14 represents a printed circuit per the layout of the same circuit as FIG. 13. However, it appears geometrically different simply because of manufacturing and production considerations associated with integrated circuit boards. At the center of FIG. 14 may be seen potentiometer R1 and, to the right and left thereof, the anode of the treatment apparatus which is termed electrode A and number 90 which is a cathode, also termed electrode B in the respective FIGS. 13 and 14. The three volt DC battery itself is shown as elements 92T an 92B in FIG. 14, 92T indicating that the top of the battery is visible from the top of the circuit board but that the bottom of the battery can only be seen if the circuit board is turned over. The most important functional electronic elements L1, Q1 and C3 are controlled by switch SW1-A by which the battery can be turned off and SW1-B by which computer 86 may be turned off.

FIG. 15 is a generic block diagram of microcontroller 16 of the type used in the present invention. As may be appreciated, a microcontroller of this type may be simply programmed given that its primary function is simply generation of pulse train 94 (see FIG. 13) having an appropriate amplitude, frequency and amperage. The microcontroller detects when battery 92 is connected and thereafter generates a pulse train of appropriate parameters responsive to the instructions that have been programmed into the program memory.

Shown is FIG. 16 is the physical arrangement of the above-described elements including treatment electrode either element 88 (anode) or element 90 (cathode). Above the electrode is an appropriate treatment pad 101 and thereabove is battery 92. Above it is the integrated circuit board of FIG. 14, which is held in place by bracket 106 such that potentiometer R1 may be placed thereabove and externally controlled through button SW1. An external housing 100 of each electrode unit is provided with openings 104 to permit escape of heat generated by the system during operation.

Figure 17:
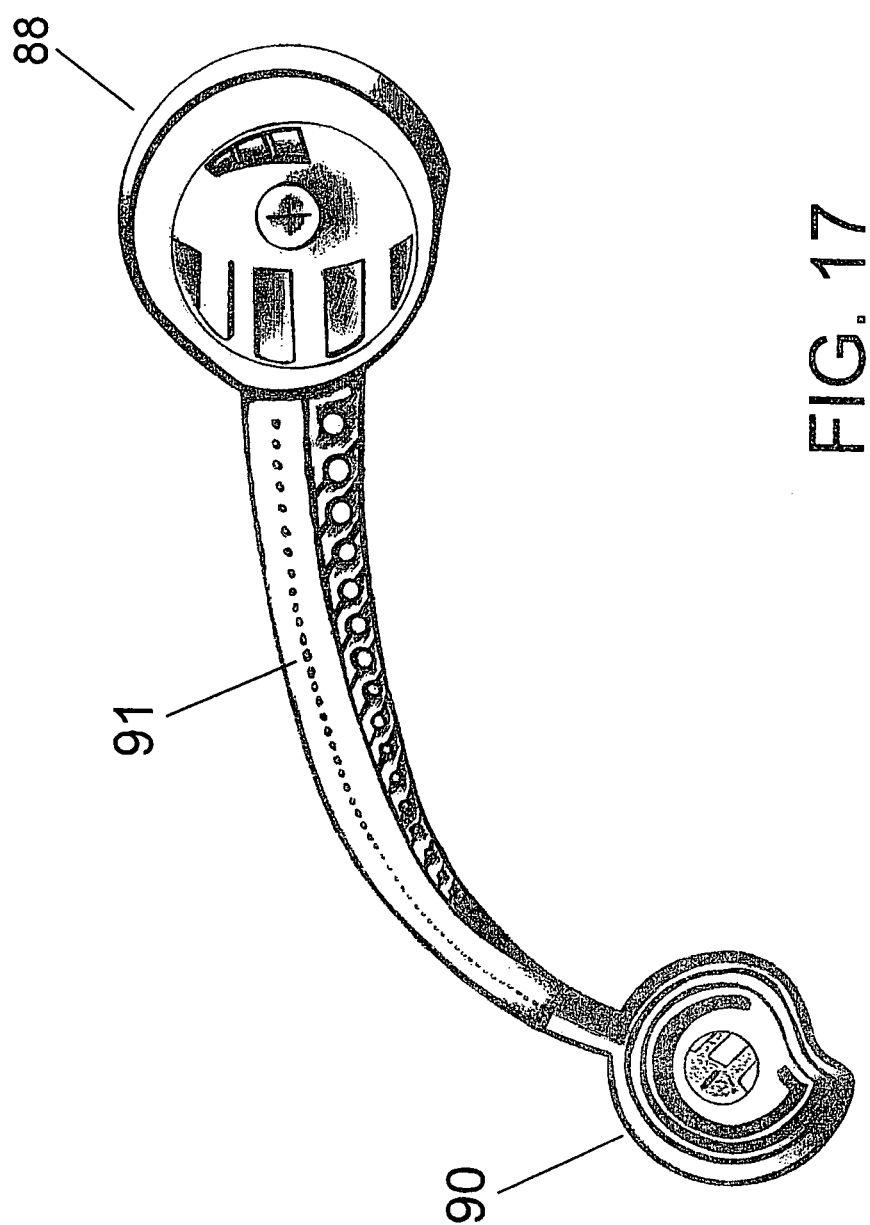
FIG. 17 is a perspective view of both electrodes and the connection therebetween used in the present inventive method.

FIG. 17 represents a rendering of the anode 88 which is integrally connected to cathode 90 by extension element 89 which must have a length in a range of about 12 to about 15 centimeters to practice the present inventive method and, in a preferred embodiment, with have a center-to-center length of about 13.8 centimeters.

As is more fully described below, anode 88 constitutes the axis or center of each treatment step, while cathode 88 is able to rotate about the anode, through the use of appropriate rotation means (not shown), thus enabling the cathode to swivel into appropriate position for the application of the neurophysiologic waveform at appropriate points within the neural system, as is more fully described below.

Figure 18:
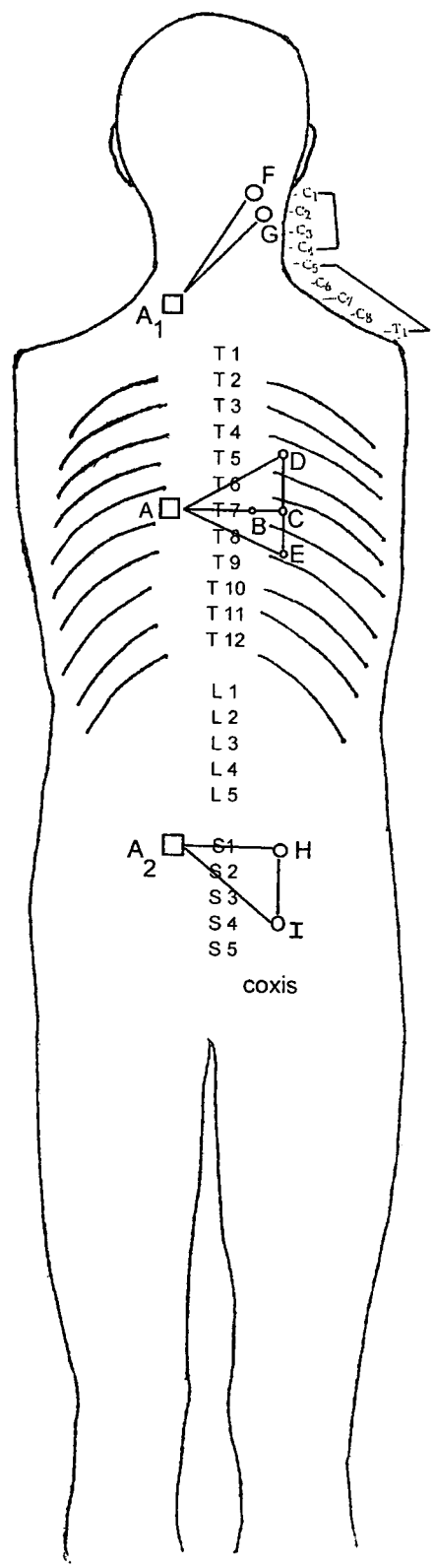
FIG. 18 is a schematic view of the neurophysiology of the human back, showing the regions of application of the device of FIG. 17.

More particularly, the device shown in FIG. 17, used with the trademark BIO (E-) LECTRICAL COMPASS, includes the anode 88 and is applied against three general areas of the neurophysiological network. The most important of these is shown at the center of FIG. 18 (and in FIG. 19) in which the letter A represents the placement of the anode relative to the T7 para-vertebrae, there being a distance of this about 4.2 centimeters from the middle of anode A to the region of right para-vertebrae T7. Therefore, the entire distance between the anode at point A and point B is about 5.2 centimeters. In other words, in the first step in the first treatment phase, the anode is placed at point A while the cathode is placed at point B. Therein, the cathode is placed at point B, shown in FIG. 12, is applied, subject to microprocessor control, from the anode to the cathode for a period of six seconds followed by an off period of two seconds. This sequence is then repeated one time following two seconds of rest. The microcontroller 86 controls these periods and succession of two application sequences.

Figure 19:
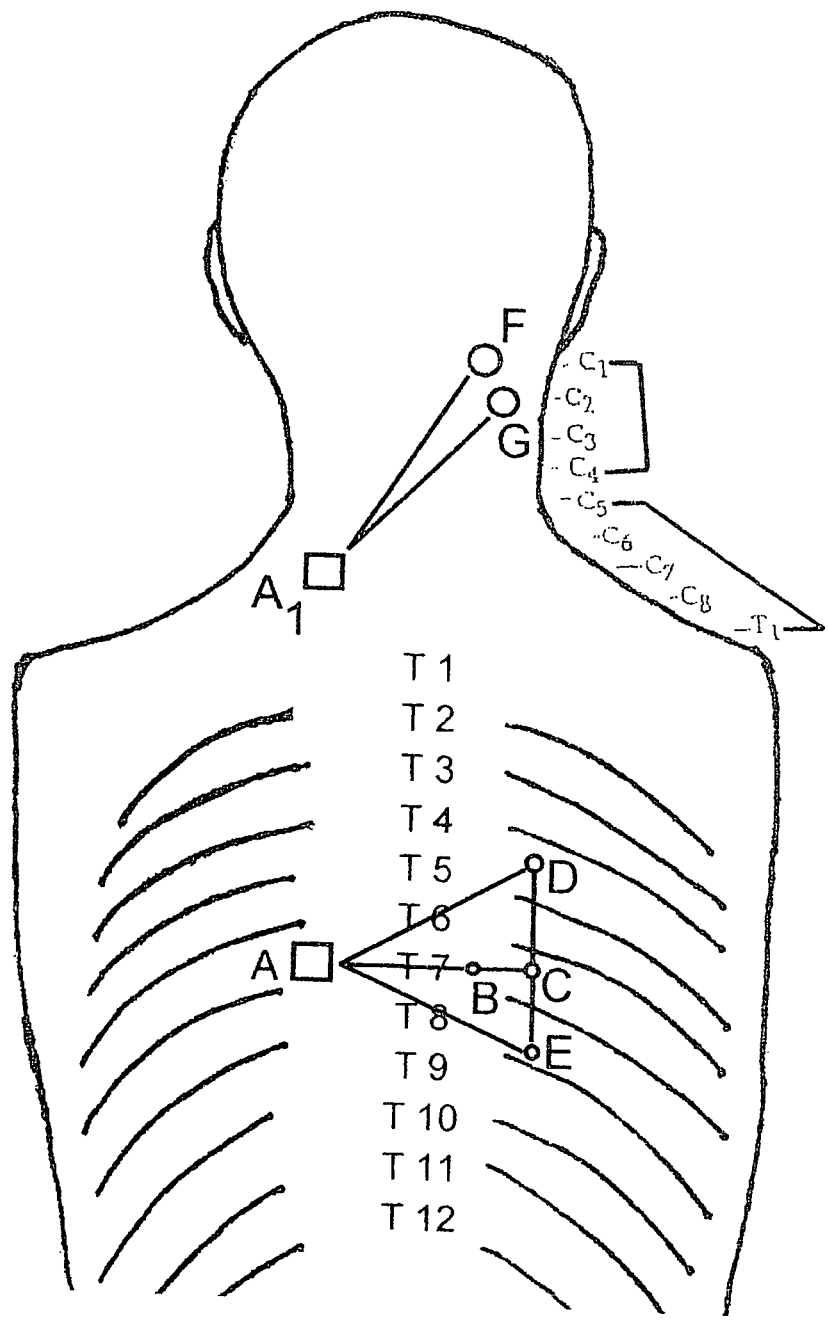
FIG. 19 is an enlarged view of the upper portion of FIG. 18.

The on/off cycle of neuro-stimulation is then repeated by placing the cathode at point C which is located within the same horizontal line defined by points A-B. However, the distance from anode A to cathode location at point C is 10.4 centimeters, that is, 5.2 centimeters to the right of the location of point B. The cycle six of seconds stimulus, followed by two seconds of rest, is then repeated for point B. All connections are determined by moving elongate extension 91 of the bio-electric compass (see FIG. 17) across thoracic vertebrae. The distance for point D is 6.5 centimeters above point C. After two cycles of 6 seconds of stimulation followed by two seconds of rest, the cathode is then moved to point E which is located 6.5 centimeters below point C. As may be noted, in the treatment of point E, the elongate extension of the bioelectric compass passes between T8 and T9 (see FIG. 19) with a total distance between point A and either of point D or E, being that of 13 centimeters. Accordingly, the length from the center of the anode, across extension 91 to the cathode must be at least 13 centimeters. In the detail of FIG. 19, one may see the neurophysiology of the area of treatment in this step of the present process. Also, as may be noted in FIGS. 1 and 2, any stimulation in the area between T6 and T8 of the SNS will inherently lead to the celiac ganglia 28 and, therefrom, will provide innervations along the celiac axis 54 (see FIG. 5) leading to the nerves of the pancreas and, in turn, its beta cells.

Figure 2:
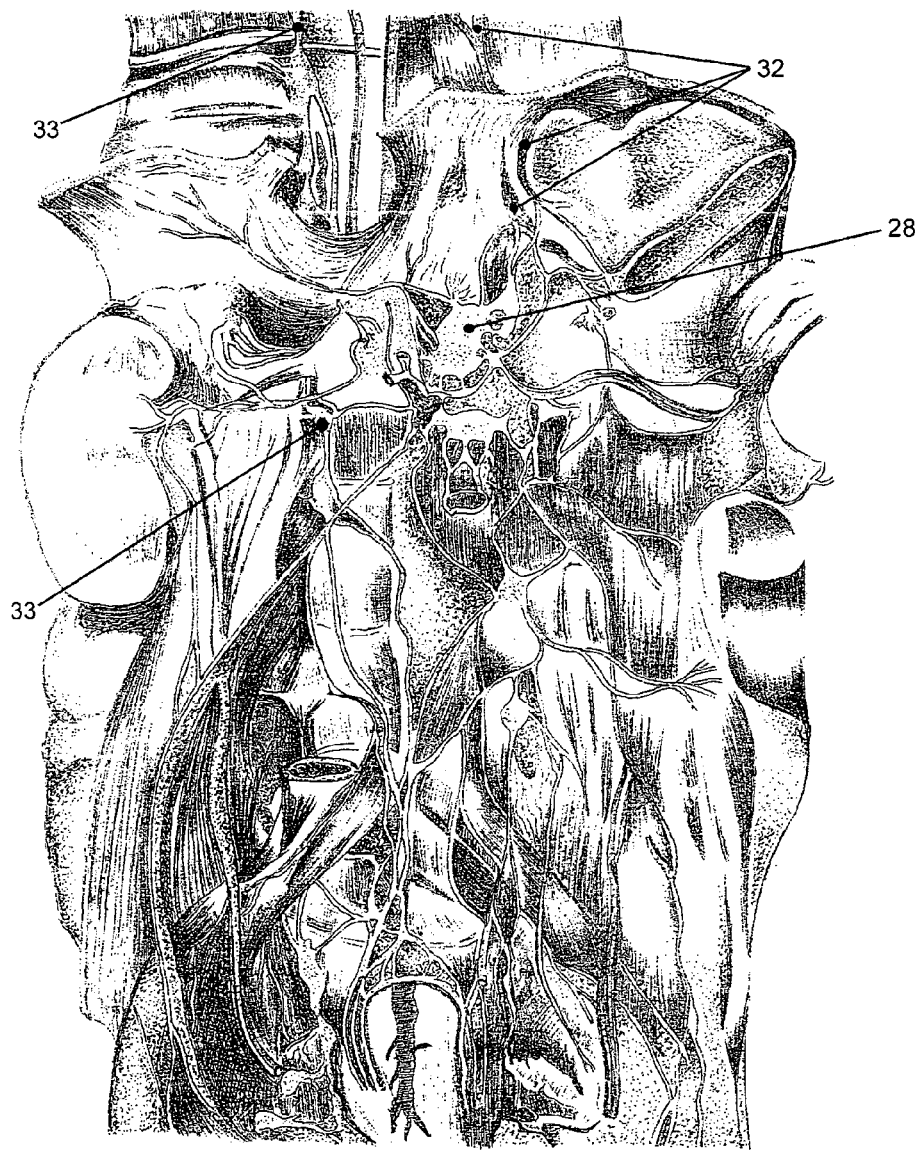
FIG. 2 is an anatomical rendering of the portions of the nervous system of the back of a human being between the neck and the pelvis.
Figure 3:
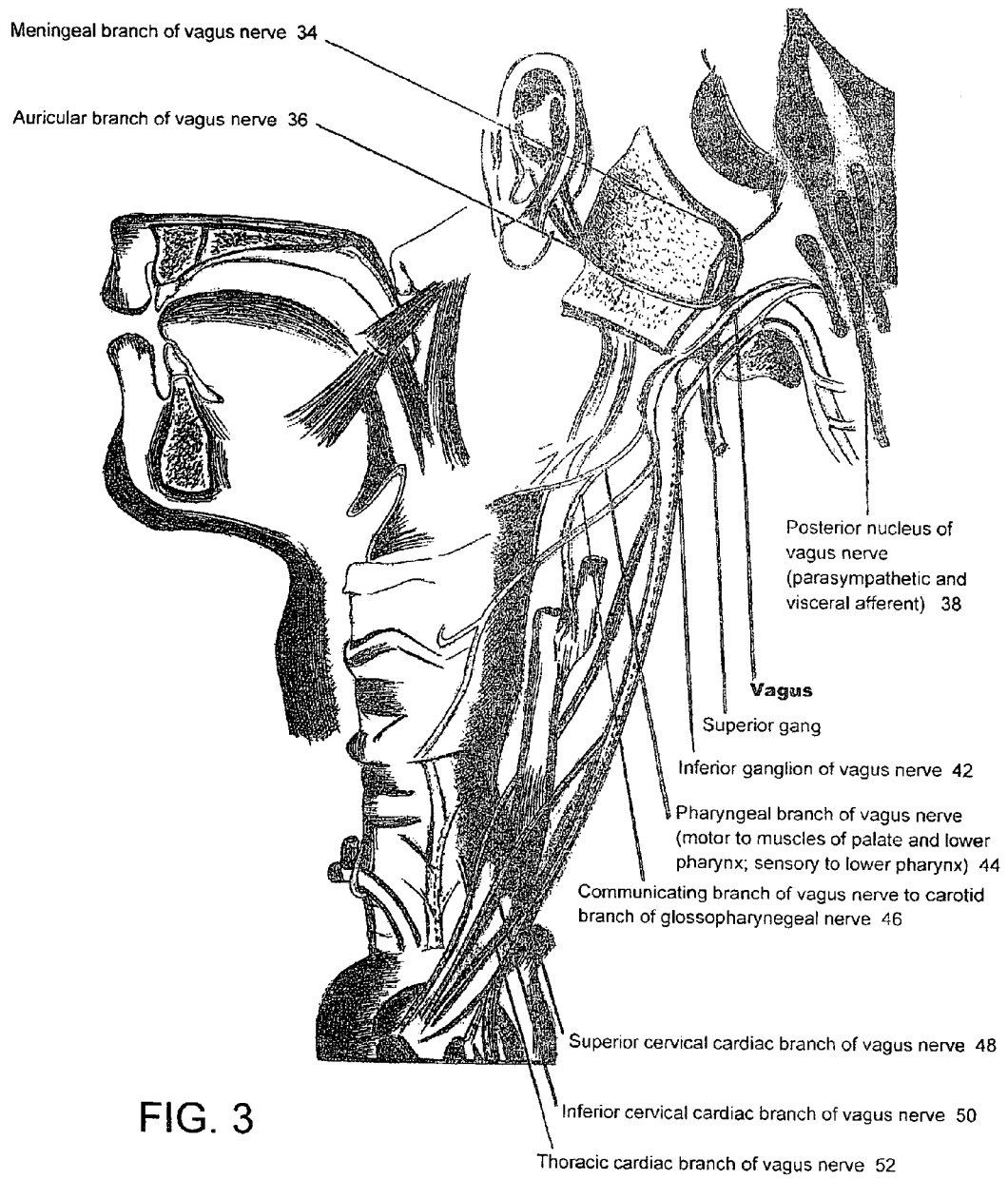
FIG. 3 is a physiologic schema of the vagus nerve and its associated efferent, afferent, and parasympathetic fibers.
Figure 4:
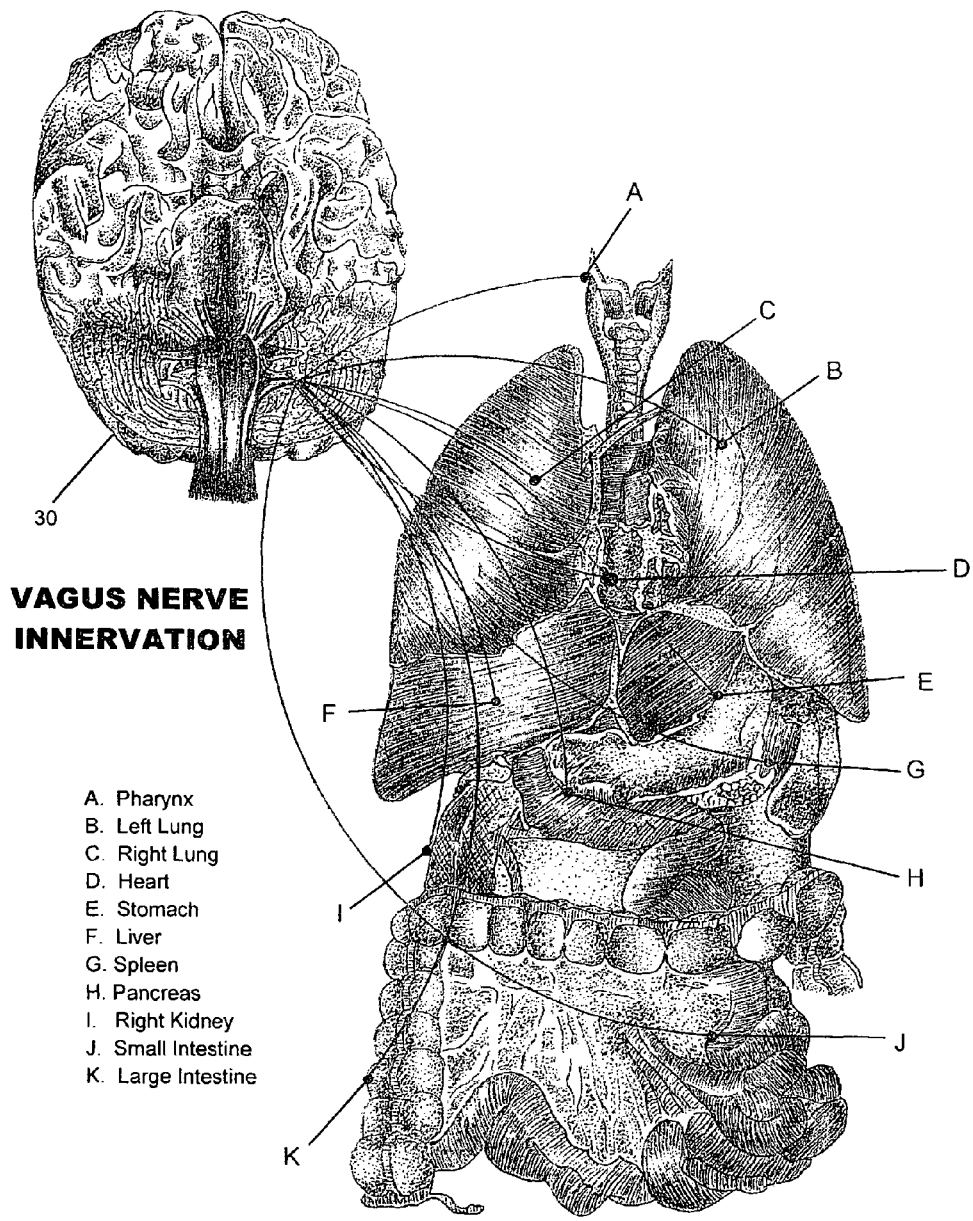
FIG. 4 is a two-part conceptual view showing the innervation of various parts of the human body by the vagus nerve.

With reference to FIGS. 18 and 19, the second step in the treatment process may be noted, that is, a treatment in the area of the neck, the primary goal of which is to provide stimulation in the area of the vagus nerve and its numerous offshoots, this as is shown in FIGS. 1, 3 and 4. Step 2 in the treatment process basically begins by placement of the anode at location A1, as shown in FIGS. 18 and 19. As may be noted, the anode at A1 is placed in the area of the trapezius muscle, while the cathode is placed in position F, which is essentially that of the primary vagus ganglion 30 (see FIGS. 3 and 4). Position F is slightly to the right of the C1 vertebrae and the entire length between A1 and F is that of 13 centimeters. Six seconds on is followed by two seconds off and then repeated. The anode is then moved to position G which is at a level of the C2 vertebrae, the distance between the anode and the cathode at this point being 13.8 centimeters, and the distance from point G to point F from which it was moved being 1.3 centimeters. At point G, the stimulation/rest cycle is twice applied. As may be appreciated, by innervations of the cervical plexus (which comprises C1 through C4), the signal of FIG. 12 will travel without interruption throughout the vagus complex stimulating, inter alia, the pancreas as well as the small intestine (see FIGS. 4 and 5).

In summary of the above, while the treatment process at points A, B, C, D and E provide innervations through the celiac complex including the celiac axis 54 into the pancreas, the treatment process at A1, F and G provides electrophysiological stimulation to the vagus nerve and its extensive neural complex as shown in FIG. 4.

Figure 20:
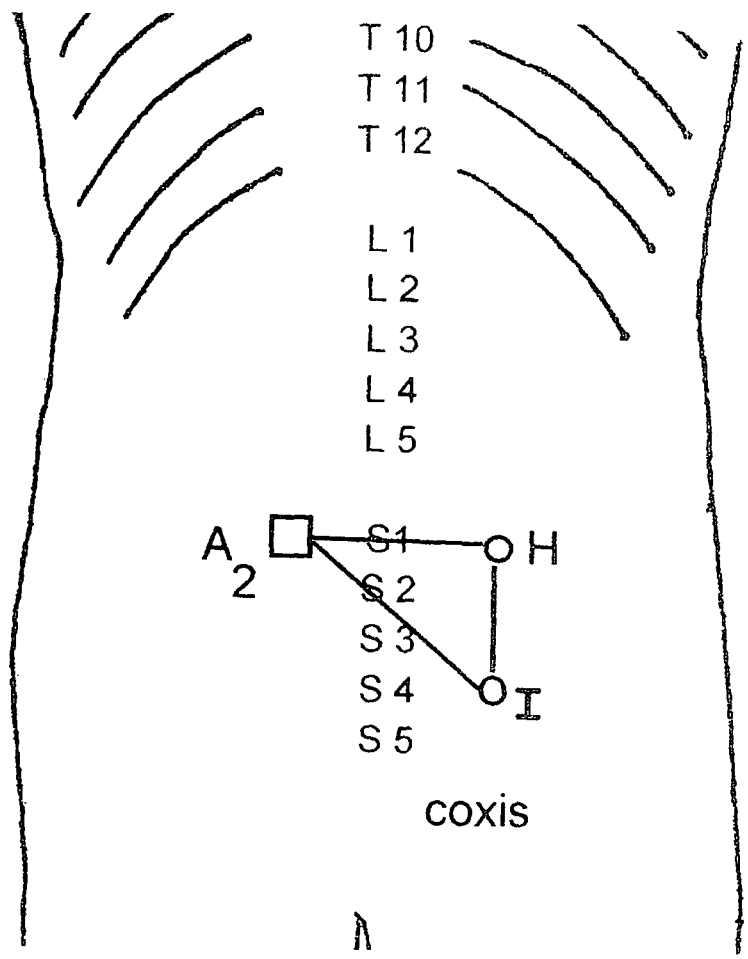
FIG. 20 is an enlarged portion of the lower back part of FIG. 18.
Figure 21:
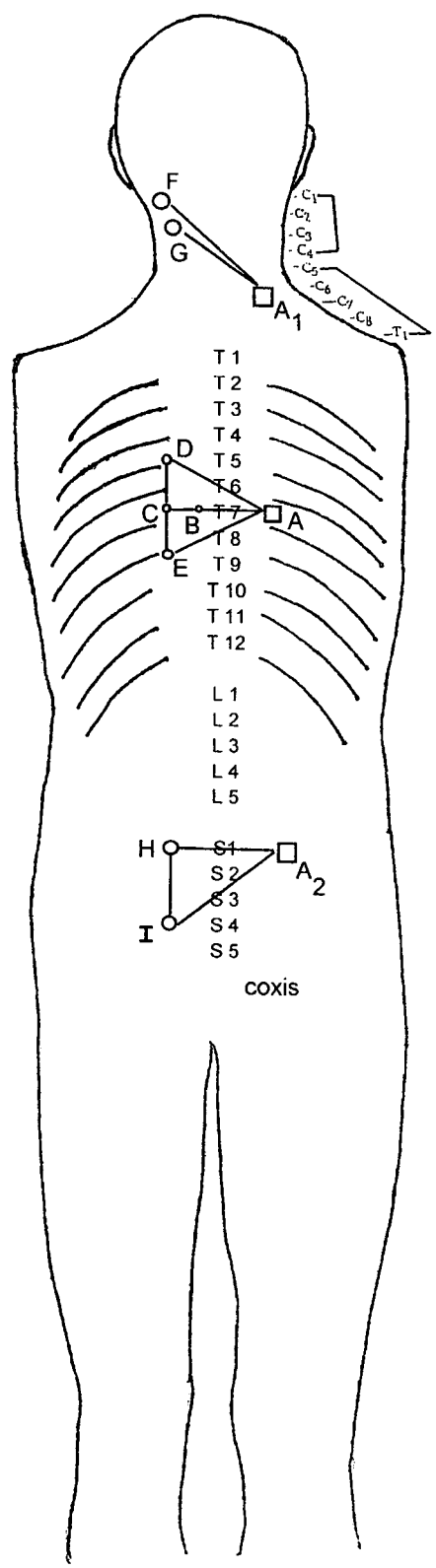
FIG. 21, is a view, similar to that of FIG. 18, however showing the utilization of the device of FIG. 17 and waveform of FIG. 12 on the left side of the back of the patient.

As the third step of the treatment protocol, the sacral area, shown in more detail in FIG. 20 is shown. Therein anode 88 is shown at A2 while the cathode which is placed at position H, the line therebetween being transverse to the S1 vertebrae of the sacral area. The distance between A2 and H is that of 7 centimeters. The on-off cycle is then twice enabled. This in turn is followed by movement of the cathode to position I. Therein the distance between the anode and cathode is 9.1 centimeters. It is noted that the distance between H and I is about 3.9 centimeters. After the steps associated with Points A, A1, and A2, as above described with reference to FIGS. 18-20, are completed, the treatment process is repeated, however, in spinal axial reversal, this as is shown in FIG. 21. In other words, in the second phase of the three-step treatment process, A, A1 and A2 are all to the right of the spinal column while points A, B, C, D, E, F, G, H and I are all to the left of the spinal column. However, in all other respects, the treatment methodology of Steps 4-6 is identical. Over a period of months, the frequency of treatment can be reduced from every other day to monthly or less. This second phase of the treatment process is to assure that equal neuro stimulation is obtained between the left and the right side of the human body and that, to the extent that the beta cells and the pancreas which have not been reached by innervations from one direction, they will be reached by innervations from the opposite direction.

Figure 22:
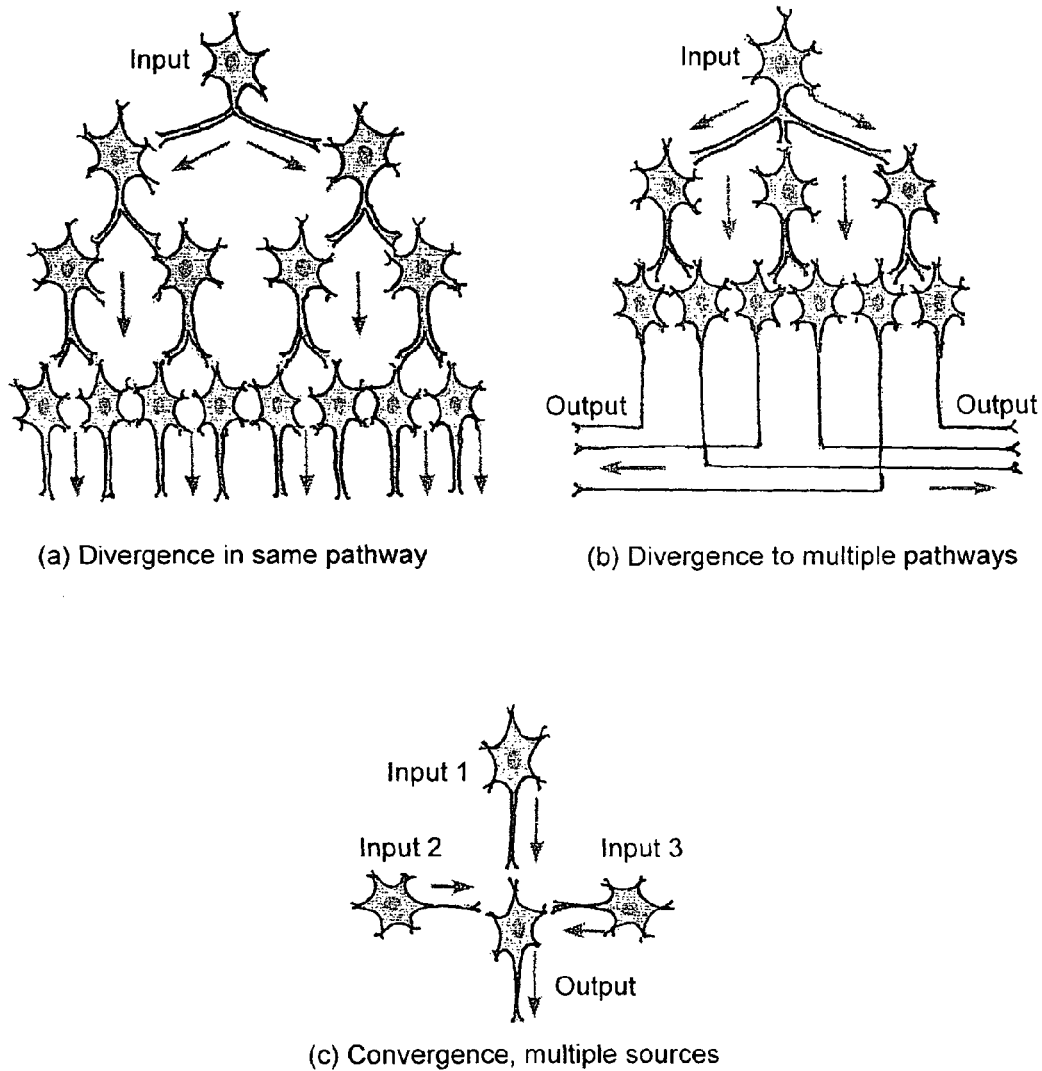
FIGS. 22 and 22A are six schematic views illustrating different forms of neural communication in the human body.
Figure 22A:
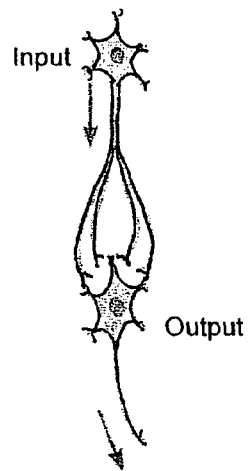
Figure 22A:
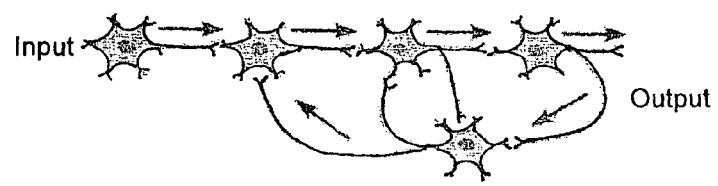
Figure 22A:
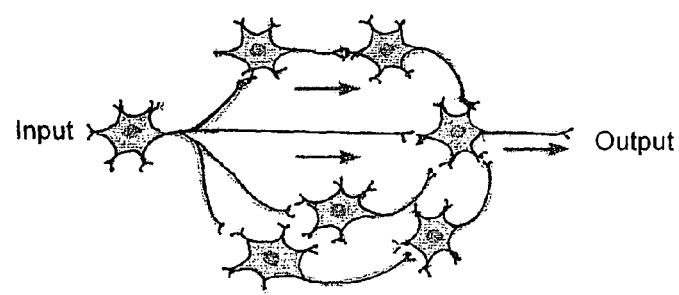

FIGS. 22 and 22A set forth a summary of the known methods by which neurons are able to electrically communicate with each other. During the pairs of six second stimulation periods above described, any of pathways a through f may be effected. However, during the two second off or rest periods, only the reverberating circuit shown in part (e) of FIG. 22A is utilized. This is know as the reverberating circuit of the human nervous system and reaches muscle layers as well as nerves and reaches muscle layers as well as the nerves. Through these electrical processes, whether occurring during the on or off period of treatment operate to facilitate the intestinal mucosa which, it is known releases cholecystokinen which in turn enables release of insulin from the beta cells. The reverberating circuit continues to function for many hours after a treatment is complete. The neural pathways shown in FIGS. 22 and 22A are also central in increasing electron activity within the efferent, afferent, and parasympathetic fibers, shown in FIG. 3, many of which are carried within the vagus nerve and its extensive complex which affects nearly every part of the human body.

Figure 7:
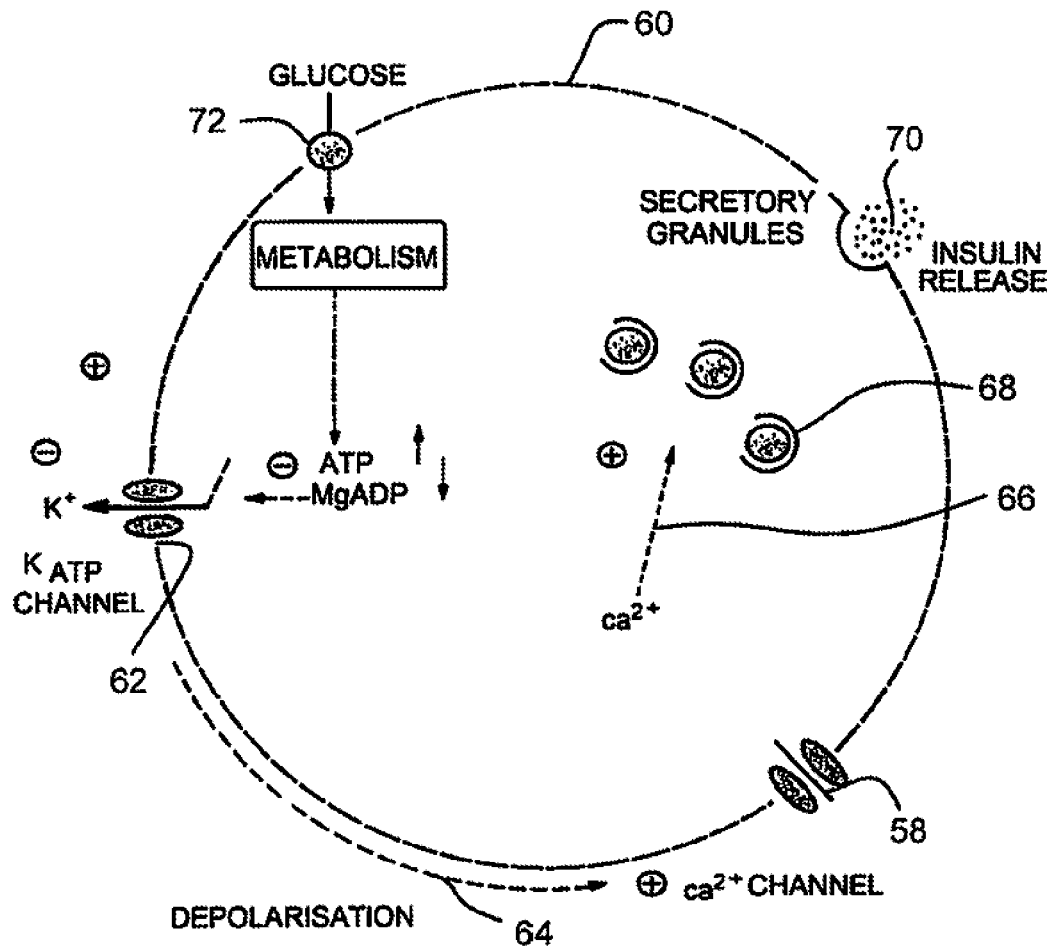
FIG. 7 is a diagrammatic view showing the role of the $Ca^{2+}$ and k plus channels in insulin secretion.
Figure 8:
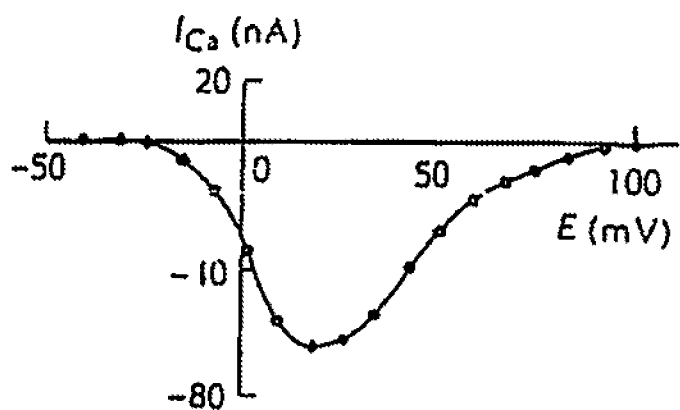
FIG. 8 is a graph showing the relationship between cell potential and calcium ion related current flow in a human cell.
Figure 9:
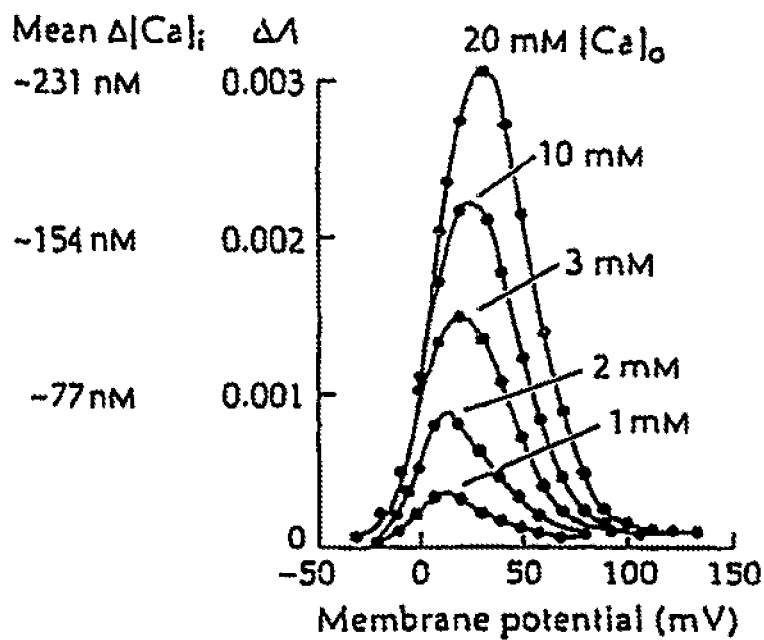
FIG. 9 is a graph showing the ratio of cell potential to concentration of free calcium ions within a cell.
Figure 10:
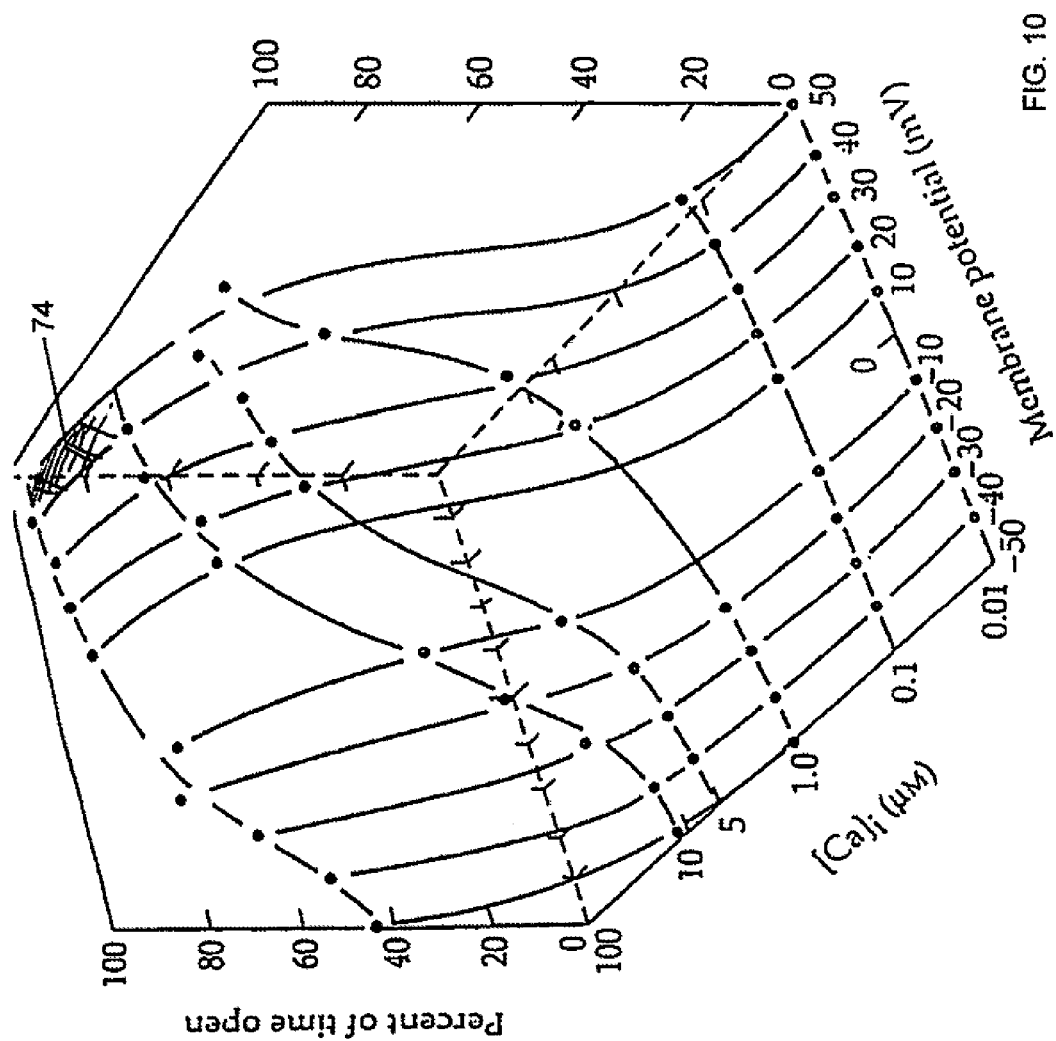
FIG. 10 is a three-dimensional graph showing the relationship between cell membrane potential, calcium ion related current flow into the cell, and percent of time that the calcium gated channels of the cells are opened.

Conceptually, the above-described neurophysiologic waveform and method of treatment operate to correct abnormal polarization and depolarization of the beta cells, shown generically in FIG. 7, such that calcium channel, potassium channel, sodium channels and other vital ionic as well as non-ionic channels are caused to open and close in a more normal fashion. Further, the negative portion 82 of the inventive electromagnetic waveform 84 and, particularly, its long capacitative extension 83 contribute to maintaining open and active ionic channels of the beta cells which would normally close much more rapidly than in any of the prior art set forth in the Background of the Invention above, whether through means implantable or of external stimulation of the body. Thereby, the healthiest possible membrane potential indicated as area 74 in FIG. 10 may be achieved for a duration sufficiently long to innervate the channels of the beta cells such that essential ions may reach them, thus enabling the release therefrom of insulin which is otherwise been blocked or handicapped by the diabetes condition TD2. The present methodology has also been found to be corrective of abnormality of the biological clock of cells which clock relates to the normal operation of channels of cell membranes.

EXAMPLE

In the course of our research, at least ten patients were studied within the last year upon whom the above-described method and novel waveform were employed. The treatments by our method, which we term the Bioelectric Compass (see FIGS. 16 and 17), were applied with respect to three ethnic groups as follows:

1. White ethnic group—2 patients.
2. Hispanic ethnic group—6 patients.
3. Afro-American ethnic group—2 patients.

At the beginning of treatment, each of the ten patients were subject to existing medication of two tablets, that is, a tablet that combines 5 mg of Janumet (sitagliptin) and 500 mg of metformin HCl, and also Lantus subcutaneous injections of 20 units of insulin per day. At the beginning of therapy, each patient was provided with specific low glucose, calorie restriction diets with a recommendation of walking between 1 and 3 miles a day. Also, at the beginning of therapy, glycemic measurements were taken before the beginning of the treatment, as above described, to compare the results to determine variables, if any, of each ethnic group so that monthly progress, over a period of a year, of each patient could be determined. See FIG. 23, top chart, column 1.

The treatment was applied in the following steps:

A. During the first month of treatment, on alternating days, between 11:00 a.m. and 8:00 p.m., for a period of five minutes, in the manner set forth above, that is, six seconds on, followed by two seconds off, and then once repeated, at each of the location groups A, A-1 and A-2, and for each side of the spinal columns as above set forth. Such every other day treatment resulted in a total of 75 minutes of aggregate application per patient during the first month of treatment, that is, fifteen applications per month at both the left and right side of the spinal column at the A, A1 and A2 location groups as explained in fuller detail above with reference to FIGS. 18 to 21.

B. During the second month of treatment, the above-described six locations of treatment was applied only two times per week, for a total of eight applications of treatment during the second month, these eight applications totaling 40 minutes of electrical treatment per patient during the second month.

C. During the third month of treatment, the regimen was applied only one time per week for a total of four applications in month 3, thus yielding a total of 20 minutes of application of the novel electromagnetic waveform during month 3.

D. During the fourth month of treatment, the treatment was applied only twice per month for each left and right side of the A, A1 and A2 cycle, thus computing to a total of ten minutes of electrical stimulation in Month 4.

In Month Five and continuing for the course of the entire year, the treatment was repeated in the same modality as explained with respect to FIGS. 18 to 21 above, but only one time per month, that is, for a five minutes treatment as the aggregate electrical stimulation to the left and right sides of the spinal column for the geometries of A, A1 and A2, as set forth.

Figure 23:
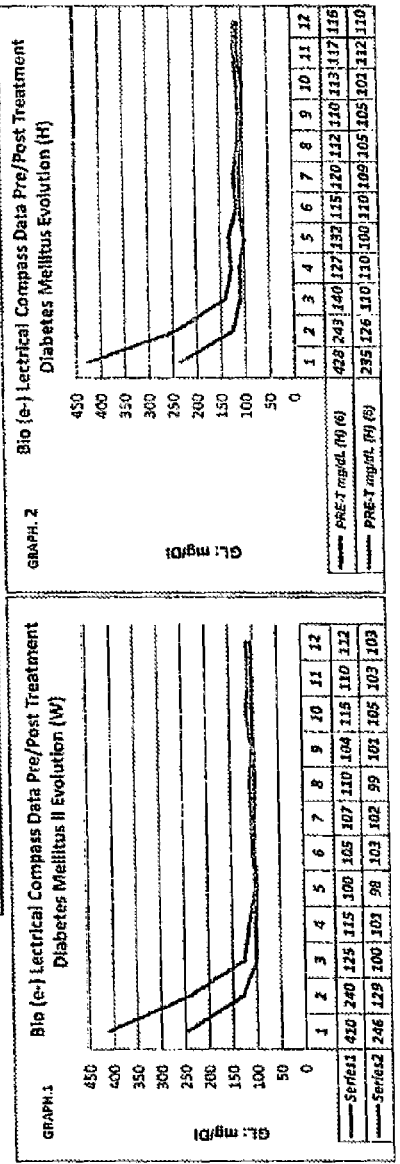
FIG. 23 are charts and graphs associated with the Example of use of the invention as set forth in the specification.
Figure 24:
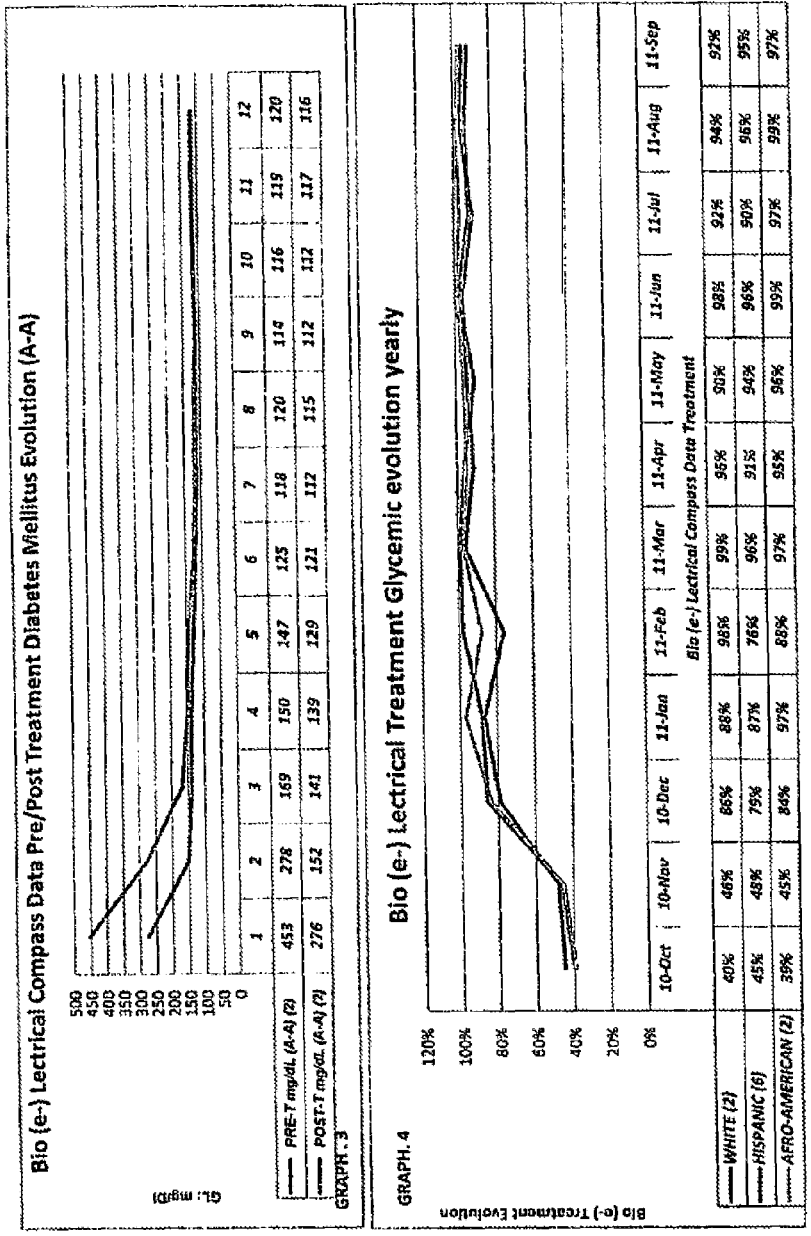
FIG. 24 are graphs showing the progress associated with the use of the present invention as described in the Example as set forth in the specification.

So that the above may be better appreciated, data resultant of the above protocol is set forth in the chart and graphs of FIGS. 23 and 24. These tables and graphs better our comprehension of the effectiveness of treatment to achieve a better conclusion.

It is noted the white ethnic group received Janumet5/500 mg and Lantus Injection 20 units before going to sleep, as set forth above. During the initiation of the treatment in the first month, the glycemic levels diminished and the Janumet medication with insulin were reduced by fifty percent. Also, one may note a descent in the glycemic 410 mg/dl level to 240 mg/dl, yielding a 40% effectiveness in the post-treatment. In addition, in the following months the Janumet and insulin were reduced to zero finishing with a complete glucose control by the fourth or fifth month, ending with glycemic data between 115 mg/dl and 100 mg/dl. See Graphs 1 and 2 of FIG. 23. As may be seen, finishing the complete year yields post-treatment results with glycemic levels of 112 mg/d, that is, totally restored beta cell function without further usage of any medication.

Finally, the other two ethnic groups experienced the same glucose controlling effect during the fourth and fifth month of treatment with the present system. Both groups also diminished their medications and insulin achieving glycemic levels between 110 mg/dl and 116 mg/dl respectably. Looking at graphs 1, 2, and 3 of FIGS. 23-24, it is clear that the effect the treatments with the method become effective by the fourth or fifth month, and then maintained a stable glycemic control level during the course of the year. As may be noted in Graph 4 (FIG. 24) the relationship of combined ethnic groups behave in the same manner as mentioned above for the particular groups.

We conclude, based on these finding the effectiveness of our method in glycemic level control and beta cell repair, that there occurs a complete regeneration of the beta cells of the pancreas, given the appearance of insulin production on the Islets and also diminishing the adverse effects of prior drugs, and medications while controlling diabetes disease complications, and having a general enhancement of metabolic regulation at a level permitting a normal healthy and comfortable lifestyle.

While there has been shown and described above the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

We claim:

1. A method for treatment of dysfunctions of a pancreas, comprising the steps of:
   (I) generating an electromagnetic signal having a sequence of asymmetric biphasic waveforms, each waveform comprising:
   (a) a voltage positive part having a pulse width in a range of about 40 to about 60 milliseconds, and including a pointed positively directed segment along a top thereof;
   (b) a voltage negative part of the waveform sharply following the positive part in a spike-like manner in a negative direction, said positive part having an interface with said negative part and a voltage drop associated with said interface between said positive and negative parts comprising a range of about 75% to about 95% of a peak-to-peak voltage of the entirety of said waveform, said peak-to-peak voltage defining a range of about 10 to about 100 volts AC, in which:
      (i) a spike-like aspect at a beginning of said negative part exhibits a pulse width in a range of about 40 to about 60 milliseconds but approaches a neutral voltage level of said waveform in a gradual manner; and
      (ii) a second aspect of said negative part of the waveform more slowly approaching said neutral level over a period of about 100 to about 200 milliseconds, prior to the initiation of the positive part of the next waveform; and
   (c) a current of said waveform defining a value in a range of about 300 to about 1000 microamperes; and
   (II) selectively applying said waveform to vagus and celiac neural complexes of a sympathetic nervous system (SNS) for defined on-off periods of time to effect delivery of said sequence of waveforms through said neural complexes to ionic channels of membranes of cells within the pancreas.

2. The method as recited in claim 1, in which:
   (a) said pulse width of said positive part preferably defines a duration of about 50 milliseconds; and
   (b) said spike-like negative aspect of said negative part of said waveform also defines a pulse width of about 50 milliseconds, while said second aspect of said negative part of said waveform exhibits a time width of about 150 milliseconds wherein a total pulse width of said waveform comprises about 250 milliseconds.

3. The method as recited in claim 2, in which a pulse width of an entirety of said waveform comprises about 256 milliseconds or a frequency of about 3.9 Hertz.

4. The method as recited in claim 1, comprising:
   placing an anode-cathode pair on either side respectively of a T6 to T8 para-vertebrae for on-off periods of about 6 and 2 seconds respectively.

5. The method as recited in claim 4, in which a distance between the anode and cathode is in a range of about 5 to about 15 centimeters.

6. The method as recited in claim 5, in which each placement is repeated twice.

7. The method as recited in claim 6, in which each placement of the method occurs every other day during a period between 1:00 a.m. and 8:00 p.m.

8. The method as recited in claim 1, comprising:
   placing of an anode-cathode pair on either side respectively of a C1 to C3 vertebrae of the neck for on-off periods of about 6 and 2 seconds respectively.

9. The method as recited in claim 4, comprising
   placing of said anode-cathode pair on either side respectively of a S1 to S3 vertebrae of the sacral area.

10. The method as recited in claim 9, in which a distance between the anode and cathode is in a range of about 5 to about 15 centimeters.

11. The method as recited in claim 10, in which each placement is repeated twice.

12. The method as recited in claim 11, in which each placement of the method occurs every other day during a period between 11:00 a.m. and 8:00 p.m.

13. The method as recited in claim 8, in which a distance between the anode and cathode is in a range of about 6 to about 16 centimeters.

14. The method as recited in claim 13, in which each placement is repeated twice.

15. The method as recited in claim 14, in which each placement of the method occurs every other day during a period between 11:00 a.m. and 8:00 p.m.

16. A system for a delivery of neurophysiologic treatment of conditions associated with an opening or closing of ionic and other channels of membranes of cells of a pancreas, the system comprising:
   a circuit configured for providing an electromagnetic signal having a sequence of asymmetric biphasic waveforms, each waveform comprising:
   (a) a voltage positive part having a pulse width in a range of about 40 to about 60 milliseconds, and including a pointed positively directed segment along a top thereof;
   (b) a voltage negative part of the waveform sharply following the positive part in a spike-like manner in a negative direction, said positive part having an interface with said negative part and a voltage drop associated with said interface between said positive and negative parts comprising a range of about 75% to about 95% of a peak-topeak voltage of the entirety of said waveform, said peak-to-peak voltage defining a range of about 10 to about 100 volts AC, in which:
(i) a spike-like aspect at a beginning of said negative part exhibits a pulse width in a range of about 40 to about 60 milliseconds but approaches a neutral voltage level of said waveform in a gradual manner; and
(ii) a second aspect of said negative part of the waveform more slowly approaching said neutral level over a period of about 100 to about 200 milliseconds, prior to the initiation of the positive part of the next waveform; and
(c) a current of said waveform defining a value in a range of about 300 to about 1000 microamperes.

17. The system as recited in claim 16, further comprising an assembly having an input in electrical communication with said sequence of waveforms, said assembly including electrodes for applying said sequence of waveforms to vagus and celiac complexes of the SNS for defined on-off periods of time.

18. The system as recited in claim 17, in which:
(a) said pulse width of said positive part preferably comprises about 50 milliseconds; and
(b) said spike-like negative aspect of said negative part of said waveform also exhibits a pulse width of about 50 milliseconds, while said second aspect of said negative part of said waveform exhibits a time width of about 150 milliseconds in which total pulse width of said waveform comprises about 250 milliseconds.

19. The system as recited in claim 18, in which a pulse width of an entirety of said waveform comprises about 256 milliseconds or a frequency of 3.9 Hertz.

20. The system as recited in claim 17 in which said assembly comprises:
an anode-cathode pair of electrodes, one each of said pair positionable at one or more of each side of a T6 to T8 para-vertebrae, each side of a C1 to C3 vertebrae of a neck, and each side of a S1 to S3 vertebrae of a sacral area, each for defined on-off periods.

21. The system as recited in claim 20, in which said defined on-off periods comprise 6 and 2 seconds respectively.

22. The system as recited in claim 20, in which a distance between an anode and a cathode of said anode-cathode electrode pair defines a dimension in a range of about 5 to about 15 centimeters.

* * * * *

UNITED STATES PATENT AND TRADEMARK OFFICE
CERTIFICATE OF CORRECTION

| | | |
|---|---|---|
| PATENT NO. | : 8,457,745 B1 | Page 1 of 1 |
| APPLICATION NO. | : 13/663658 | |
| DATED | : June 4, 2013 | |
| INVENTOR(S) | : Garcia et al. | |

It is certified that error appears in the above-identified patent and that said Letters Patent is hereby corrected as shown below:

On the Title Page, Item 54 and in the Specifications, Col. 1
TITLE: Change "Homeostatis" to -- Homeostasis --.

On the Title Page, Item 57
ABSTRACT, Last Line: Change "about 1000" to -- about 10,000 --.

In the Drawings

In Fig. 13 of the Drawings: The notation "100 KOHM" next to the designator "R4" at the right of the figure is deleted.

In the Specifications

Column 11, Line 20: Change "about 1000 microamps" to -- about 10,000 microamps, the maximum varying as a function of the bio-reactance of the patient --.

Column 14, Line 43: Change "70" to -- about 10,000 --.

Column 21, Line 21: Change "about 1000" to -- about 10,000 --.

In the Claims

Column 22, Line 28: Change "1" to -- 11 --.

Column 23, Line 14: Change "about 1000" to -- about 10,000" --.

Signed and Sealed this
Twenty-eighth Day of January, 2014

Michelle K. Lee
*Deputy Director of the United States Patent and Trademark Office*